(12) United States Patent
Lee et al.

(10) Patent No.: US 10,513,543 B2
(45) Date of Patent: Dec. 24, 2019

(54) ANTIGEN CHIMERA, ANTIGEN COMPOSITION, VACCINE, METHOD OF PREPARING THE SAME AND CASSETTE THEREOF

(71) Applicant: SHANGHAI UNITED CELL BIOTECHNOLOGY CO., LTD.

(72) Inventors: Keryin Lee, Shanghai (CN); Yuhong Geng, Shanghai (CN)

(73) Assignee: SHANGHAI UNITED CELL BIOTECHNOLOGY CO., LTD., Shanghai (CN)

(*) Notice: Subject to any disclaimer, the term of this patent is extended or adjusted under 35 U.S.C. 154(b) by 0 days.

(21) Appl. No.: 15/102,125

(22) PCT Filed: Jul. 30, 2014

(86) PCT No.: PCT/CN2014/083291
§ 371 (c)(1),
(2) Date: Jun. 6, 2016

(87) PCT Pub. No.: WO2015/081711
PCT Pub. Date: Jun. 11, 2015

(65) Prior Publication Data
US 2016/0368951 A1 Dec. 22, 2016

(30) Foreign Application Priority Data

Dec. 6, 2013 (CN) .......................... 2013 1 0655338
May 20, 2014 (CN) .......................... 2014 1 0217707

(51) Int. Cl.
| | | |
|---|---|---|
| C07K 14/205 | (2006.01) |
| A61K 39/108 | (2006.01) |
| A61K 39/02 | (2006.01) |
| C07K 14/245 | (2006.01) |
| C07K 14/28 | (2006.01) |
| A61K 39/00 | (2006.01) |

(52) U.S. Cl.
CPC ........ *C07K 14/205* (2013.01); *A61K 39/0258* (2013.01); *A61K 39/107* (2013.01); *C07K 14/245* (2013.01); *C07K 14/28* (2013.01); *A61K 2039/55544* (2013.01); *A61K 2039/6037* (2013.01); *C07K 2319/00* (2013.01); *C07K 2319/40* (2013.01); *C07K 2319/55* (2013.01); *Y02A 50/474* (2018.01); *Y02A 50/484* (2018.01)

(58) Field of Classification Search
None
See application file for complete search history.

(56) References Cited

U.S. PATENT DOCUMENTS

| 7,544,361 B2 * | 6/2009 | Arakawa ................ A61K 39/12 |
| | | 424/186.1 |
| 2006/0246087 A1 | 11/2006 | Arakawa et al. |
| 2008/0274143 A1 | 11/2008 | Daniell |
| 2013/0058969 A1 | 3/2013 | Daniell |

FOREIGN PATENT DOCUMENTS

| AU | 2006309281 A1 | 12/2007 |
|---|---|---|
| CN | 1563388 A | 1/2005 |
| CN | 1890374 A | 1/2007 |
| CN | 1973903 A | 6/2007 |
| CN | 101036786 A | 9/2007 |
| CN | 101062015 A * | 10/2007 |
| CN | 101987873 A | 3/2011 |
| CN | 102151332 A | 8/2011 |
| CN | 102260353 A | 11/2011 |
| CN | 102604993 A * | 7/2012 |
| CN | 102675466 A | 9/2012 |
| CN | 103127498 A | 6/2013 |
| EP | 1522585 A1 | 4/2005 |
| EP | 1650225 A1 | 4/2006 |
| EP | 2397547 A1 | 12/2011 |

(Continued)

OTHER PUBLICATIONS

Chen et al. Adv Drug Deliv Rev. Oct. 15, 2013: 65(10);1357-1368.*

(Continued)

*Primary Examiner* — Oluwatosin A Ogunbiyi
(74) *Attorney, Agent, or Firm* — Harness, Dickey & Pierce, P.L.C.

(57) ABSTRACT

The present invention provides an antigen chimera, comprising: a fusion protein of an antigen and a mucosal immune adjuvant protein monomer capable of forming a multimer; and the mucosal immune adjuvant protein monomer capable of forming the multimer; wherein the mucosal immune adjuvant protein monomer capable of forming the multimer is one selected from cholera toxin B subunit (CTB) and *E. coli* heat-labile enterotoxin B subunit (LTB), the multimer is a pentamer, and in the chimera the molar ratio between the fusion protein and the mucosal immune adjuvant protein monomer capable of forming multimers is 1:4. In the present invention, a characteristic that a mucosal immune adjuvant protein can form a pentamer is used to form a chimeric structure, so as to form an antigen having a higher potency. Moreover, a mucosal immune adjuvant protein is used to improve an immune effect, so as to improve an effect of enhancing antigen immunogenicity. In addition, the chimeric protein antigen formed with the recombined antigen of the present invention stimulates a mucous membrane to produce secretory IgA and induce the occurrence of mucosal immunity.

9 Claims, 12 Drawing Sheets

Specification includes a Sequence Listing.

(56) References Cited

FOREIGN PATENT DOCUMENTS

| JP | 2005-052135 A | 3/2005 |
|---|---|---|
| JP | 2008-500008 A | 1/2008 |
| WO | 2005033317 A1 | 4/2005 |
| WO | 2010092963 A1 | 8/2010 |
| WO | 2013041966 A1 | 3/2013 |

OTHER PUBLICATIONS

Giudice et al. Annu. Rev. Immunol. 2001, 19:523-63.*
Uniprot Accession No. P69996 "UreB" Jan. 4, 2005, 5 pages.*
Uniprot Accession Q1CUQ9 "NAP" Jul. 11, 2006 4 pages.*
Weltzin et al. Infection and Immunity, May 2000, vol. 68 No. 5, p. 2775-2782.*
Chinese Office Action for Application No. 201410217707.8 dated Mar. 10, 2015, and its English translation thereof.
European Search Report for Application No. 14868697.5, dated Apr. 6, 2017.
International Preliminary Report for Application No. PCT/CN2014/083291, dated Jun. 16, 2016.
Japanese Office Action for Application No. 2016-557173, dated Apr. 13, 2017, and its English translation thereof.
Wang, Jing et al. "Study on immunoregulatory functions of *E. coli* heat-liable enterotoxin B subunit", Institute for Cancer Research School of Life Science and Technology, Xi' an Jiaotong University, Xi'an 710061, China, 19(2), 2003.
Zhang, Bao-hua et al. "Advance on the immuno-adjuvant of cholera toxin B subunit", Journal of Shangqiu Teachers College, College of Life Science, Hebei Normal University, Shijiazhuang 050016, China, 17(6), Dec. 2001.
Chinese Search Report for Application No. 2014102177078 dated Feb. 28, 2015, and an English concise explanation of relevance thereof.
Australian Office Action for Application No. 2014360050, dated Dec. 6, 2013.
Canadian Office Action for Application No. 2,932,211, dated Mar. 1, 2017.
Chinese Search Report for Application No. 201410217707.8 dated Nov. 20, 2014, and its English translation thereof.
International Search Report and Written Opinion of the ISA for PCT/CN2014/083291, ISA/CN, Haidian District, Beijing, dated Nov. 4, 2014.
Korean Office Action for Application No. 10-2016-7018064 dated Mar. 28, 2018, and its English translation thereof.
Canadian Office Action for Application No. 2,932,211, dated Apr. 5, 2018.
Baldauf, Keegan J. et al. "Cholera Toxin B: One Subunit with Many Pharmaceutical Applications"; Toxins : ISSN 2072-6651, Mar. 20, 2015.
Weltzin et al., "Parenteral Adjuvant Activities of *Escherichia coli* Heat-Labile Toxin and Its B Subunit for Immunization of Mice against Gastric Helicobacter pylori Infection", Infection and Immunity, vol. 68, No. 5 May 2000, p. 2775-2782.
European Office Action for Application No. 14868697.5 dated Oct. 15, 2018.
Korean Office Action for Application No. 10-2016-7018064 dated Sep. 21, 2018, and its English translation thereof.
Mudrak B, Kuehn MJ. "Heat-Labile Enterotoxin: Beyond GM1 Binding". Toxins 2010, 2, 1445-1470.
Bäckström M1, Shahabi V, Johansson S, et al. "Structural basis for differential receptor binding of cholera and *Escherichia coli* heat-labile toxins: influence of heterologous amino acid substitutions in the cholera B-subunit". Mol Microbiol. May 1997;24(3):489-97.
English Translation of Japanese Office Action for Application No. 2016-557173 dated Oct. 23, 2017, Feb. 23, 2018.
European Search Report for Application No. 14868697.5 dated Sep. 20, 2017.
Yongjun, Feng et al. "Stepwise Disassembly and Apparent Nonstepwise Reassembly for the Oligomeric RbsD Protein", National Laboratory of Protein Engineering and Plant Genetics, College of Life Sciences, and The Center for Protein Science, Peking University, Beijing; Mar. 2006.
Wiseman, R. Luke et al., "Partitioning Conformational Imtermediates between Competing Refolding and Aggregation Pathways: Insights into Transthyretin Amyloid Disease", Department of Chemistry and the Skaggs Institute of Chemical Biology, The Scripps Research Institute; Sep. 2005.
European Office Action for European Application No. 14868697.5, dated May 7, 2019.
Mudrak, Benjamin et al. "Heat-Labile Enterotoxin: Beyond $G_{M1}$ Binding"; Toxins, vol. 2, No. 6, (Jun. 14, 2010), pp. 1445-1470, XP55584696.
Baeckstroem M. et al.: "Structural Basis for Differential Receptor Binding of Cholera and *Escherichia coli* Heat-Labile Toxins: Influence of Heterologous Amino Acis Substitutions in the Colera B-Subunit", Molecular Microbiology, vol. 24, No. 3, (Jan. 1, 1997), pp. 487-497, XP000992487.

* cited by examiner

ANTIGEN CHIMERA, ANTIGEN COMPOSITION, VACCINE, METHOD OF PREPARING THE SAME AND CASSETTE THEREOF

This application is a U.S. National Phase application under 35 U.S.C. § 371 of International Application No. PCT/CN2014/083291, filed Jul. 30, 2014, entitled "ANTIGEN CHIMERA, ANTIGEN COMBINATION, VACCINE, METHOD OF PREPARING THE SAME AND KIT THEREOF", which claims the benefit of and priority to Chinese patent applications 201310655338.6, filed Dec. 6, 2013 and 201410217707.8, filed May 20, 2014. The entire contents of of all of the above applications are incorporated by reference herein.

TECHNICAL FIELD

The present invention relates to the field of immunization, particularly to mucosal immune antigen, vaccine and preparation methods and cassettes thereof.

BACKGROUND OF THE INVENTION

Mucosal immune system is widely distributed under mucous membrane of the respiratory tract, gastrointestinal tract and urogenital tract and within the lymphoid tissue at some of the exocrine glands, and is a main place for performing local specific immune function.

Since more than 95% of the body-associated infections occurs in the mucous membranes or happened by invading the body through mucous membranes, so mucous membrane is the largest portal for pathogens to invade the body. Currently, the main infectious diseases those with great hazard for animal life and health as well as those with great difficulties to be controlled, such as influenza, tuberculosis, glanders, and salmonellosis, belong to the mucous membrane invading-through or mucosa-associated diseases, and the resulting mucosal injury and disorders of the mucosal immune function, often become an important mechanism of opportunistic pathogen infection, or even tumorigenesis.

Mucosal immune system is the first immune barrier for the body against invading pathogens, and this independent immune system with distinctive structure and function has a positive meaning for the prevention of pathogen colonization and invasion. Unlike traditional systematic immune system, mucosal immune system comprises the diffuse lymphoid tissue consisted of the large number of immune cells and immune molecules as dispersed in the mucosa epithelium or submucosal lamina propria, or a mucosa-associated lymphoid tissue formed by a single or multiple aggregated lymphoid follicles. More than 50% of the lymphoid tissue of the body and more than 80% of the immune cells concentrated in the mucosal immune system. Furthermore, the antibodies in the mucous secretions are mainly secretory sIgA and sIgM antibodies. Mucosal immune system can be divided into two parts by function thereof: inductive site and effective site. Communication between the inductive site and the effective site occurs primarily through homing of lymphocytes. The main function of the mucosal immune system is to recognize and respond to a large number of a wide variety of antigens inhaled or ingested from the mucosal surface. The mucosal immune system not only can reduce the immune response to a large number of harmless antigens or generate tolerance to the same, but also can generate highly efficient humoral immunity and cellular immunity to those harmful antigen or pathogen and perform effective immune rejection or removal.

Mucosal immunity is theoretically the most effective routes of immunization to prevent those pathogens which cause pathogenic role by mucosal infection, because in other ways of immunization, it is difficult to induce significant mucosal immune response by vaccines. However, so far, most of the vaccines which have been approved or are in clinical studies still use the injection route for immunization, only a few of them use route for mucosal immunity. To study the reason, in addition to the difficulties for detection of the local mucosal immune specific antibody, the main difficulties plaguing the development of mucosal immunity vaccine product are, for the role of the body's host defense, during the mucosal immunity it cannot accurately control the level of the antigens into the body as that when in the injection immunization way. After oral or topical administration, antigens reach mucosal surface and then will undergo a dilution by mucous secretion, mucus gel adsorption, protease/nuclease hydrolysis and being cleared by the endometrial barrier. Only very few amount of antigen can go through the mucosa into the body, to play an effective mucosal immune response. In general, the mucosal uptaking rate for those water-soluble antigens and antigens without mucosal function is low, and part of them might cause immune tolerance phenomenon in the intestines. The most effective method to solve the low mucosal uptaking rate is to mimic the features of natural mucosal pathogens and apply effective mucosal adjuvant, as well as enhance the level of combination with mucosal surface of the body (preferably selectively adhered to the M cells). More effective mucosal vaccines are still needed.

SUMMARY

In order to improve the immunogenicity of antigens for mucosal immunity, the present invention provides an antigen chimera, comprising: a fusion protein of an antigen and a mucosal immune adjuvant protein monomer which capable of forming a multimer, and the mucosal immune adjuvant protein monomer capable of forming said multimer, wherein the mucosal immune adjuvant protein monomer capable of forming the multimer is one selected from cholera toxin B subunit (CTB) and E. coli heat-labile enterotoxin B subunit (LTB), the multimer is a pentamer, and in the chimera the molar ratio between the fusion protein and the mucosal immune adjuvant protein monomer capable of forming multimers is 1:4, wherein the pH in which the chimeric antigen is stable is greater than 7.0, preferably pH 8.0. Both of CTB and LTB are very effective mucosal immune adjuvant, and are capable of forming a stable pentamer. The antigen chimera prepared using this nature, not only can keep its mucosal immune adjuvant properties, but also increases the volume of antigen, so as to be easily taken by the antigen presenting cells (APC), and further improve stimulation of the mucosal immune system and systemic immunity. Furthermore, the stability of the chimeras is closely related to pH value. In the present invention, the pH for the stable presence of the antigen chimera is greater than 7.0, preferably is pH 8.0. The chimera, under this condition, in particular the chimera formed from the CTB pentamer, can most effectively enhance mucosal immune effect.

In one embodiment of the invention, CTB and LTB of the antigen chimera are in their natural structure or a mutant capable of forming the pentamer. Compared with the CTB and LTB from eukaryotic expression with the occurrence of glycosylation, the CTB and LTB and mutant thereof expressed by prokaryotic expression vector has a natural structure, and can more effectively stimulate an immune response to the antigen, and present its function of an adjuvant.

In one embodiment of the invention, the antigen in the antigen chimera has a molecular weight in the range of 10 to 100 kD, preferably 16 kD to 65 kD. In the range of 10-100 kD, the antigens can better ensure CTB or LTB folded into the correct conformation, and be easily to form a stable pentamer. When the molecular weight of the antigen is too small, it might be affected by CTB or LTB, and then the fusion protein might be promoted to form multimers of the fusion protein itself, and thus cannot be correctly folded. If the molecular weight is too large, steric hindrance might occur to hinder the formation of LTB or CTB pentamer.

In an embodiment of the present invention, the antigen may be an antigen suitable for the mucosal immune, especially those antigens from pathogens infecting the human or animal body via mucosal routes, including, but not limited to, H. pylori antigens, typhoid antigens, influenza HA antigens.

In a preferred embodiment of the present invention, the H. pylori antigen is at least one selected from Helicobacter pylori urease B subunit (UreB), Helicobacter pylori cytotoxin associated gene A (CagA) and neutrophil activating protein (NAP). These antigens are strong immunogenic, non-toxic, and thus are good candidate antigens for vaccine.

In an embodiment of the present invention, the fusion protein comprises a three G4S (Gly-Ser-Ser-Ser-Ser: SEQ ID No 4) linkers located between the antigen and the mucosal immune adjuvant protein monomers. The addition of this flexible linker could avoid protein interactions between the antigen protein and CTB or LTB during the renaturation by refolding, and thus contribute to the formation of the correct conformation.

The present invention also provides an antigen composition comprising the antigen chimera as described above, wherein said pH in which the antigen chimera is stable is greater than 7.0, preferably is pH 8.0.

The present invention also provides a vaccine comprising said antigen composition and excipients suitable for vaccine. Preferably, the vaccine is an oral vaccine, a vaccine for nasal administration or a vaccine for rectal administration.

The present invention also provides a cassette for preparing the antigen composition, comprising a vector expressing the above fusion protein and a vector expressing the mucosal immune adjuvant protein monomer capable of forming multimers. Preferably, the vectors are all prokaryotic expression vectors.

The present invention also provides a method for preparing the antigen chimera, said method comprises expressing the fusion protein, and the mucosal immune adjuvant protein monomer capable of forming multimers respectively with the vectors in the above-mentioned cassette, then combining these two proteins to form the chimera via a renaturation method, wherein said renaturation method comprises the renaturation of the two proteins by co-locating them in refolding solution containing urea and DTT (or mercaptoethanol). Preferably the concentration of urea in the refolding solution is 1.0M to 2.5M. The concentration of DTT or mercaptoethanol is 0.2 mM to 1.0 mM.

The present invention also provides a process for preparing a chimera by renaturation, the chimera comprising (1) a fusion protein of a protein with a protein monomer capable of forming a multimer and (2) the protein monomers capable of forming the multimer, the chimera is formed by fusion of the protein monomers of (1) the fusion protein and (2) the protein monomers to form the multimer, the method comprising:

The (2) protein monomers capable of forming a multimer are pre-refolded in a buffer solution containing 6M to 9M, preferably 8M, of urea, and with a pH of 3.0 to 4.0 for 0.5 to 3 hours, preferably pre-refolded for 1 hours; and The (1) fusion protein and (2) protein monomers capable of forming the multimers are refolded in a refolding solution containing 1.0M to 2.5M urea and 0.2 mM to 1.0 mM of DTT or mercaptoethanol for the formation of the chimera.

Preferably, the pH of the refolding solution is greater than 7.0, more preferably the pH of the refolding solution is 8.0.

In the present invention, we have chosen to maintain a certain concentration of urea and DTT (or mercaptoethanol) in the refolding solution, which can effectively prevent the formation of homo-pentamer of the monomeric proteins capable of forming multimer themselves. Furthermore, under the certain pH conditions, the formation of chimeras can be promoted, and the chimera assembly efficiency can be improved, which effectively overcome the defect of low assembly efficiency occurred in the conventional renaturation procedure. The renaturation method may be used in a plurality of areas in need of forming protein chimera which is not limited to the field of vaccines described herein.

DETAILED DESCRIPTION

In order to more clearly illustrate the present invention, it will be described in detail in the following for various preferred embodiments of the present invention, as well as the technical effect of the embodiments.

The present invention provides an antigen with enhanced immunogenicity and its preparation method. On the one hand, the immune response is strengthened through the use of mucosal adjuvant; on the other hand, feature of forming pentameric CTB or LTB is used to improve the mucosal immune adjuvant effect, as well as increase the volume of antigen, so as to be easily ingested by APC, and thus be more conducive to the occurrence of an immune response. Further, the present inventors chose to maintain a certain concentration of urea and DTT (or "urea and mercaptoethanol") in the refolding solution, which can effectively prevent the formation of homo-pentamers of the monomer capable of forming pentamer, thus contributing to the chimera forming, and the efficiency of assembling chimera may be improved. The defect of low assembly efficiency of the chimera occurred in the conventional renaturation condition is overcome effectively.

Aspects of the present invention will now be described in more detail from several aspects, including the selection of immune adjuvant, the selection of antigens, and refolding methods.

About the Immune Adjuvant

In order to enhance the immunogenicity of an antigen, the present invention selected LTB or CTB, respectively, to be used with the antigen and form a new antigen composition.

Figure 1:
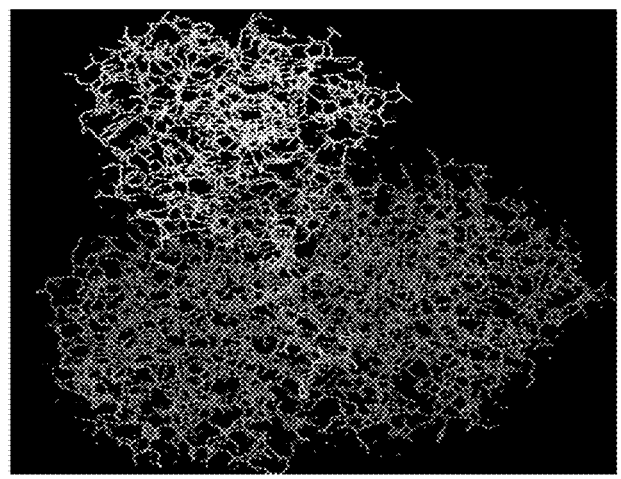
FIG. 1 is a computer simulation perspective configuration view of cholera toxin (CT)
Figure 2:
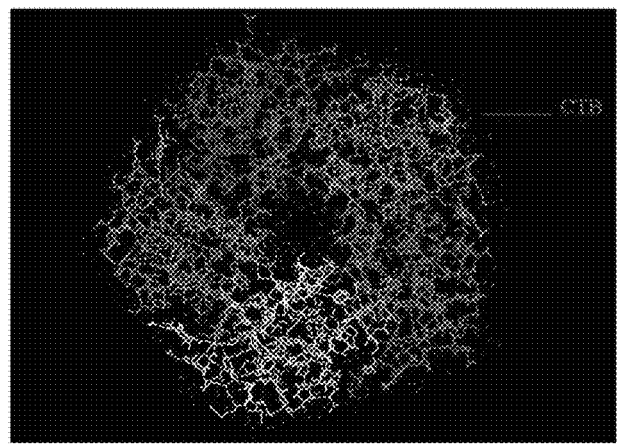
FIG. 2 is a computer simulation perspective configuration view of CTB homo-pentamer.

Cholera toxin is a potent mucosal immune adjuvant consisting of an A subunit and five B subunits (see FIG. 1) components. The 5 B subunits are non-covalently bound together to form a very compact and stable cylindrical-shape pentamer (see FIG. 2). B subunit monomers have a side chain of three anti-parallel sheets on each side thereof. In the pentamer the adjacent monomers interact each other via the sheets and a lot of salt bonds, thereby the B-subunit pentamer becomes one of the most stable protein complexes. CTA is an active part of the cholera toxin, while CTB is non-toxic and its main function is to combine with sialic acid ganglioside (GM1) on the mammalian intestinal epithelial cells and makes the CTA to enter into cells to produce an immune response. CTB has a strong immunogenicity, because in addition to it could improve the rate of the intestine tract uptaking the oral vaccine assisted by it through binding GM1, CTB can also specifically affect the tight junction or zonula occludens structure among small intestinal mucosa cells, so as to increase permeability, prevent oral vaccine being digested in the small intestine mucosa and to maintain the antigenicity, thereby enhancing the titer of antibodies produced by the body, so that a good immune response could be produced in the body. Nowadays CTB is deemed as one of the most effective and safest mucosal immune adjuvant so far.

LTB is efficient mucosal immune adjuvant too. *Escherichia coli* heat-labile enterotoxin (LT) is a heat-labile periplasm exotoxin secreted by the enterotoxigenic *Escherichia coli* cell into the periplasm. LT is a $AB_5$ type protein hexamers consisting of A subunit with ADP-ribosyltransferase activity as well as B subunits in combination with ganglioside, wherein the A subunit is the primary unit of its toxicity, B-subunit has immunogenicity and adjuvant functions. LT not only is immunogenic, but also is an effective mucosal adjuvant, can significantly enhance the body IgA and IgG response against the candidate antigen, while reduce the body's immune tolerance to the candidate antigens and induce long-term memory against them. Therefore, mucosal adjuvant LTB has been widespread concerned as a mucosal adjuvant.

The present invention provides a recombinant antigen composition comprising: a fusion protein of an antigen with CTB or LTB monomer; and the corresponding CTB or LTB monomer protein. By using the feature of non-covalently binding of five CTB or LTB monomers, a chimeric structure of said fusion protein with the four corresponding monomeric CTB or LTB complex could be formed, thereby increasing the effective volume of the antigen, and being easy uptaken by APC. Meanwhile, it is known that CTB and LTB are potent immune adjuvants that can reduce the body's immune tolerance to the candidate antigens and thus could effectively play its role in promoting immunity. And since the formation of the chimeric proteins of the antigen with five CTB or LTB monomers, an antigen with higher potency has been formed, thereby the immunogenicity of the entire antigen composition is enhanced.

About Antigen

In order to better play the role of mucosal immunity, the antigens of pathogens which are infected via mucosa are preferable for the invention, including but not limited to *H. pylori* antigens, typhoid antigen, and influenza HA antigen. By using the chimeric antigens prepared of the present invention, the immunogenicity of antigens can be enhanced, which will help to develop a more effective vaccine.

Hereinafter *Helicobacter pylori* are used as an example to describe in detail and validated technical solutions and technical effects of the present invention.

*Helicobacter pylori* (HP) is a micro-aerobic gram-negative bacterium parasitized on gastric epithelial cell surface, firstly isolated in 1983 by the Australian scholar Marshall and Warren from human gastric mucosa. HP can colonize and survive in acidic environment, make the body produce inflammation and immune response, damage gastric mucosal barrier, so that cause the imbalance between gastric epithelial cell apoptosis and proliferation. HP is an important pathogen for human gastrointestinal disease and is the main cause of chronic gastritis, gastric ulcer and duodenal ulcer. In 1994, WHO has confirmed that it's closely related with gastric cancer, and listed it as A class carcinogen. HP is one of the world's highest prevalent bacteria, it was reported that 90% of Asians and 60% of Europeans infected with HP, so the prevention and treatment of HP infection has become the focus of global attention.

Currently in clinical two or triple antibiotic treatment is generally used to treat HP infection. But obviously there are the following shortcomings: 1) generation of drug-resistant strains; 2) easy to relapse and re-infection; 3) high adverse reactions and expenses; 4) cannot achieve population control effect, and cannot effectively control the spread and infection of HP. Therefore, the development of the vaccine with clear effect for the prevention and control of HP infection is very important. HP vaccines currently being studied mainly include whole-cell vaccines, subunit vaccines (genetically engineered vaccine), live vector vaccines and DNA vaccines. Most of the studies use whole-cell HP or whole bacteria lysates, or HP-toxic proteins such as urease, vacuolating cytotoxin, CagA, neutrophil-activating protein alone or in combination with different adjuvants for inoculation, in animal models all of them can cause protective responses.

Preventive vaccine play a role by the body's immune responses, so by selecting a valid HP antigen to immunize the body, the body can be stimulated to produce a protective immune response, and thus the vaccine could play a role in protecting the body from infection of HP. With in-depth technical study of the pathogenesis of HP as well as the development of molecular biology—the construction and application of genetic engineering strain provides for effective antigen screening favorable conditions, as well as the prevention and eradication of HP infection has taken a crucial step.

Figure 3:
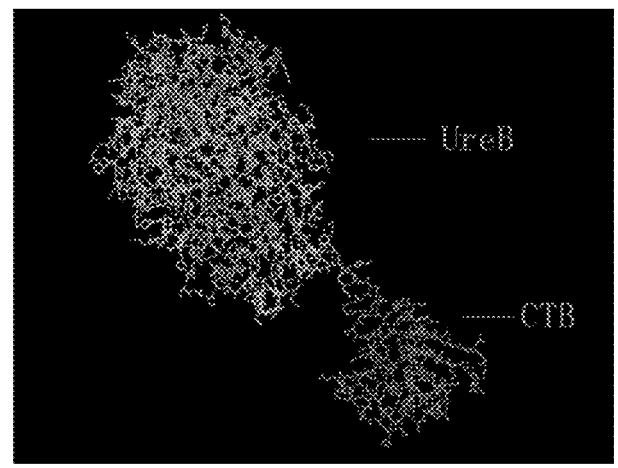
FIG. 3 is a computer simulation perspective diagram of the CTB-UreB fusion protein.
Figure 4:
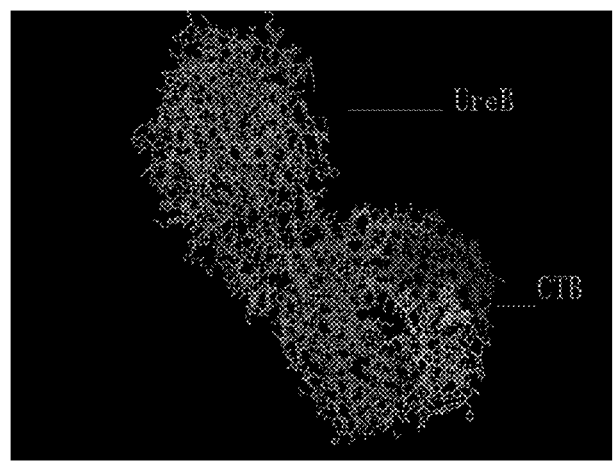
FIG. 4 is a computer simulation perspective configuration view of the CTB-UreB/4CTB chimeric proteins.

Take the preparation of *Helicobacter pylori* vaccine as an example, the inventors prefer the *Helicobacter pylori* urease, *Helicobacter pylori* CagA protein and *Helicobacter pylori* NAP as an effective antigen for *Helicobacter pylori*. The present invention applied genetic bioengineering techniques, prepared three fusion proteins of HP antigens and CTB (CTB-X (X=UreB, CagA, NAP)) (see FIG. 3), and by use of characteristics that the five CTB non-covalently bound characteristics, chimeric structure CTB-X (X=UreB, CagA, NAP)-4CTB is formed (see FIG. 4), thereby forming an antigen with higher potency via the chimeric protein of HP antigens and 5 CTB monomer, and conducted relevant animal immunogenicity experiments for verification.

Urease

In the colonization and infection process, Urease (Ure) HP has effects of decomposition of urea, neutralizing stomach acid, and is important for pathogenicity HP. HP urease is both a colonization factor and a virulence factor. Urease gene is jointly owned by all HP strains, which encodes a protein with strong urease activity. Urease distributes on HP surface, accounts 5 to 10% of the whole amount of the total bacterial protein. Currently it is found that gene size of urease is about 7.5 kb, there are total nine open reading frame (ORF), i.e. UreA, UreB, UreC, UreD, UreE, UreF, UreG, UreH and UreI. Wherein UreA and UreB are two structural urease subunits which are highly conserved, they are often selected as target genes in PCR detection of HP infection and candidate gene vaccine.

UreB is a major component of the outer membrane antigen of HP, is produced by encoding 569 amino acid residues, and is the strongest protective antigen protein in HP, with non-toxic, strong antigenic characteristics and relatively conservative. In the pathogenic process of HP, it plays a key role. By comparing among different strains, it is found that the urease B subunit has a homology of more than 97.9%, indicating that the variation of HP UreB antigen among different HP strains is minimal. In addition, the main active part of UreB locates on cell surface thereof, and its large molecular weight and particulate structure facilitates mucosal immunization, thus urease molecules can be used as a reasonable choice for a vaccine antigen. Meanwhile in vivo HP surface has adhesion characteristics for cytoplasmic protein, could release urease from autolysis to the surface of live cell, which also provided an important theoretical basis for the HP vaccine research. The experiment confirmed that administration of UreB protein vaccine via route of mucosal immunization can induce and stimulate the body's protective immune response, indicating UreB is important candidate protective antigens for HP infection. It is also the preferred antigen for genetically engineered vaccine, and has significant advantage.

A lot of literature reported that, by oral immunization of mice which previously infected cats gastric *Helicobacter* (*Helicobacter Felis*, Hf) with recombinant urease subunit B (rUreB), it is found that in the mice not only the Hf infection was eliminated, but also re-infection in mice could be prevented; Kleanthous et al. used rUreB plus mucosal adjuvant LT for mice immunization, found that as compared with the control group: in the group of immunized mice urease activity in the stomach decreased significantly, and gastric tissue quantitative culture showed that more than 97% of HP were reduced; Michetti et al conducted a clinical study on the safety and immunogenicity of different oral doses (180 mg, 60 mg, 20 mg, 4 times/day) of urease and LT (5 µg), found that: all volunteers were tolerated, and the vaccine could reduce stomach HP colonization, thus reducing the degree of gastritis; Saldinger et al. used cholera toxin (CT) in combination of rUreB to immune BALB/c mice which previously infected with Hf, and found that: in all mice in the immunization group, Hf had been eradicated; further analysis revealed proliferation of the spleen $CD^{4+}$ T cells, increased serum IgG1, accompanied by increased IL-4 and reduced IFN-γ, so it is supposed that rUreB may induce a Th2 $CD^{4+}$ T cells proliferation which could help remove HP. Some scholars conducted phase I clinical trials on HP infected volunteers by immunization with UreB in combination with LT, also found a significant reduction in the density of HP infection. Lee et al conducted similar studies on other non-human primates and also showed that reducing the density of the stomach HP could help reduce the degree of gastritis. However Solnick reported an immunization study on rhesus monkeys with urease via oral and intramuscular administration, followed by HP challenging test, and found: although UreB is capable of inducing humoral immunization, but all rhesus monkeys given with HP challenges were infected with HP, and bacterial density was not statistically significant in the experimental group and the control group. These results indicate that the present UreB related HP vaccine is still not perfect, needs further study.

CagA Protein

CagA gene also known as cytotoxin-associated gene, its gene expression product is CagA protein. As a toxin secreted by the bacteria, it is transferred by type IV secretion system Cag pathogenicity island (PAI) from bacteria to host cells and is phosphorylated to involve in signal transduction in a host cell and cause rearrangements of cytoskeletal structures. Studies have shown that, cagA positive HP is a virulent strain of HP, is closely related to atrophic gastritis, gastric cancer and peptic ulcers and other common gastrointestinal diseases. The expressions of CagA in more than 90% of clinical isolated HP were positive. Nearly all types of the HP having CagA gene expresses CagA protein, and induce a measurable antibody response. According to the literatures, CagA-positive strains are capable of directly or indirectly (via NF-KB) inducing gastric epithelial cells to secrete IL-8, and IL-8 play an important role in neutrophil chemotaxis and activation processes, can cause gastric mucosal injury. Animal experiments found that CagA gene and CagA protein have a good correlation with gastritis, peptic ulcer, especially gastric cancer. Marchetti et al use the model by immunization HP infection mouse with recombinant CagA, showed that an induced protective immune response could be generated and protection rate reached 70%. Crabtree et al applied recombinant CagA as an antigen, to immune via the stomach to mice which chronically infected with HP, succeeded cleared HP, and the mice were effectively protected from re-infection. It suggested that CagA as protective antigen for HP vaccine has higher feasibility, but the protective effect of this antigen is limited to those strains producing CagA, and no protective effect will be generated for those strains not producing CagA. It can be seen that there is no satisfactory vaccine for CagA protein either now.

NAP

Evans et al found one kind of NAP in HP water-soluble extract, which can raise and activate neutrophils, promote neutrophil adhesion to gastric epithelial cells, activate neutrophils to release reactive oxygen metabolites, and lead to inflammation lesions of the gastric mucosa.

NAP is highly conserved. It is found in clinical studies that specific antibodies against NAP can be found in 60% of serum samples from the HP infected patients. NAP is a ferritin, the gene encoding the same could be detected in almost all kinds of HP, but there is a great difference in NAP activity after in vitro expression. It could interact with endothelial cell adhesion molecules (ICAM-1) through CD11a/CD18 and CD11b/CD18, leading to the adhesion between leukocytes and endothelial cells. It has a function of selective combining acidic glycosphingolipids of neutrophil and further regulating leukocyte function, and could combine with mucin so as to provide possibility for HP colonization in gastric epithelial cells. Therefore NAP play an important role in the adhesion and the pathogenic process of HP. Satin et al immunized 10 mice with purified recombinant NAP via oral immunization, the results showed eight mice acquired protective immunity. It suggests that NAP can be used as effective protective antigens for vaccines against HP infection.

In a preferred embodiment of the invention, the present invention provides a recombinant *H. pylori* antigen composition comprising a fusion protein of *Helicobacter pylori* antigen with CTB monomer, and CTB monomer. By means of properties of CTB monomer could form pentamers with itself, the size of the antigen is increased, and is easily ingested by APC. In addition, CTB is a good immune adjuvant. Thus, recombinant *H. pylori* antigen composition of the present invention can effectively enhance the immunogenicity of *H. pylori* antigens, which will help develop a more effective vaccine.

In a further embodiment, the antigen is selected from at least one of *Helicobacter pylori* UreB protein, *Helicobacter pylori* CagA protein and NAP. These antigens are all non-toxic, with strong immunogenicity and relatively conservative antigen among currently known *H. pylori* antigens, and are more suitable for use in vaccines.

Selection of the Combination Mode of Antigen and Immune Adjuvant

Routine immunoadjuvants generally are used by being mixed directly with an antigen, and then administered simultaneously with the antigen to stimulate the immune response, but the effect of adjuvants to enhance the immunogenicity of the antigen is not ideal. The present invention prepares a fusion protein of an antigen and mucosal immune adjuvant protein monomers, then a chimeric protein is formed by non-covalent between the fusion protein and the mucosal immune adjuvant protein monomer, thus not only its mucosal immune adjuvant properties are maintained, but also the volume of antigen is increased, so as to be easier uptaken by antigen-presenting cells.

For the preparation of the fusion protein, in the present invention a flexible protein linker was added between the antigen and CTB (or LTB), such that after the fusion the folding of the antigen and CTB (or LTB) will not be affected each other, and form the correct conformation respectively. In one embodiment, the present invention selected a 3 G4S linker. However, the present invention is not limited to use of such a linker, and other linkers, such as a spiral form linker peptide (A (EAAAK) nA: SEQ ID No. 5), and glucose aureus protein A (PA), also can be used in the present invention.

Further, on the basis of ensuring the conformation of the two parts, especially that of CTB (or LTB), it may be conducive to form the proper formation of pentamers and be advantageous for the pentamer formation efficiency.

Preparation Method for the Antigen Chimeras

The present invention also provides a cassette comprising a vector expressing the fusion protein of said antigen and CTB (or LTB) and a vector expressing the corresponding mucosal immune adjuvant protein CTB (or LTB). As known to those skilled in the art, in addition to the protein of interest, the expression vector should also comprise elements necessary for expression of the protein of interest, such as a promoter, terminator, optional marker genes, etc.

The expression vector is preferably a prokaryotic expression vector, for example, prokaryotic vectors such as pET series. Methods and reagents for preparing the protein of interest with prokaryotic expression vector are known in the art, it can be found in commonly used reference books in the art, for example, Cold Spring Harbor Laboratory compiled "Molecular Cloning: A Laboratory Manual" ((US) J. Sambrook et al, translated by Huang PeiTang et al, Beijing, Science Press), "Cell Laboratory Manual" ((US) D L Spector et al. translated by Huang PeiTang et al, Beijing, Science Press) and the like.

For the preparation of chimeras, it has been part of a technical problem. How to avoid the monomers forming homo-pentamer before forming the chimeras with the fusion protein is the key point for the chimeras yield. Generally, most protein expressed with a prokaryotic cell will form inclusion bodies, and need to be solved with a solution of urea after washing. The protein solved by the urea solution is basically in a denaturation state, in which it is hard to produce its native conformation. However, the conventional refolding process is the gradual process of urea's removal, so as to refolding it gradually to form a correct conformation. Regarding the monomer capable of forming a multi-mer, in the process of the removal of urea, it is easy to spontaneously form homo-multimers themselves rather than a hetero-multimers with the monomer in the infusion protein. Therefore, when the chimeras are produced with the conventional method, the yield is very low.

The present inventors chose to maintain a certain concentration of urea and DTT (or "urea and mercaptoethanol") in the refolding solution, so as to be capable of effectively preventing the formation of homo-pentamers from the monomers themselves, promoting the formation of the chimeras, and improving the assembly efficiency of the chimera. Thus the defect of lower assembly efficiency resulted from the conventional renaturation is effectively overcome.

The present invention also provides a process for preparing a chimera by renaturation, the chimera comprising (1) a fusion protein of a protein with a protein monomer capable of forming a multimer and (2) the protein monomers capable of forming the multimer, the chimera is formed by fusion of the protein monomers of (1) the fusion protein and (2) the protein monomers to form the multimer, the method comprising: the (2) protein monomers capable of forming a multimer are pre-refolded in a buffer solution containing 6M to 9M, preferably 8M, of urea, and with a pH of 3.0 to 4.0, for 0.5 to 3 hours, preferably 1 hour; and the (1) fusion protein and (2) protein monomers capable of forming the multimers are refolded in a refolding solution containing 1.0M to 2.5M urea and 0.2 mM to 1.0 mM of DTT or mercaptoethanol for the formation of the chimera.

Unlike the conventional refolding solution, the present invention uses a refolding solution with a certain concentration of urea and reductive reagent, so that the fusion protein and the protein monomers could be recombined to a desired chimera during the slowly refolding process. In the preferable process, the pre-refolding is conducted under a certain pH condition, and then in the presence of a reductive reagent, at lower concentrations of urea the fusion protein and the protein monomers were slowly refolded, a high yield of chimeras is obtained unexpected.

For a large scale production, the yield will directly affect the cost of production, even directly impact on the possibility of large-scale production. By use of the method of the present invention, the yield of chimeras can reach the levels for mass production.

Next the preferred embodiments of the present invention are described below through detailed descriptions of specific examples.

1. Preparation of Antigen 1.1 Example 1 Preparation of CTB-UreB/4CTB 1.1.1 Construction of the Recombinant Engineering Bacteria: PET-28a-CTB-UreB BL21-DE3
1.1.1.1 Construction of the Fusion Gene CTB-UreB:

DNA sequence of UreB is derived from HP strain MEL-HP27, DNA sequence of CTB is derived from *Vibrio cholerae* 0395, a (G4S)$_3$ linker sequence (italics and underlined) rich in glycine/serine and having a flexible property is introduced into the fusion DNA fragment between sequences of UreB and CTB, and CTB-UreB codons are synthesized.

The gene sequence thereof is SEQ ID No. 1:

```
ATGACACCTCAAAATATTACTGATTTGTGTGCAGAATACCACAACACACA      50

AATACATACGCTAAATGATAAGATATTTTCGTATACAGAATCTCTAGCTG     100
```

-continued

```
GAAAAAGAGAGATGGCTATCATTACTTTTAAGAATGGTGCAACTTTTCAA      150

GTAGAAGTACCAGGTAGTCAACATATAGATTCACAAAAAAAAGCGATTGA      200

AAGGATGAAGGATACCCTGAGGATTGCATATCTTACTGAAGCTAAAGTCG      250

AAAAGTTATGTGTATGGAATAATAAAACGCCTCATGCGATTGCCGCAATT      300

AGTATGGCAAAT***GGTGGTGGTGGTTCTGGTGGTGGTGGTTCTGGTGGTGG***      350

*TGGTTCT*ATGAAAAAGATTAGCAGAAAAGAATATGTTTCTATGTATGGCC      400

CTACTACAGGCGATAAAGTGAGATTGGGCGATACAGACTTGATCGCTGAA      450

GTAGAACATGACTACACCATTTATGGCGAAGAGCTTAAATTCGGTGGCGG      500

TAAAACTTTGAGAGAAGGCATGAGCCAATCCAACAACCCTAGCAAAGAAG      550

AACTGGATTTAATCATCACTAACGCTTTAATCGTGGATTACACCGGTATT      600

TATAAAGCGGATATTGGTATTAAAGATGGCAAAATCGCTGGCATTGGCAA      650

AGGCGGCAACAAAGACATGCAAGATGGCGTTAAAAACAATCTTAGCGTGG      700

GTCCTGCTACTGAAGCCTTAGCTGGTGAAGGTTTGATCGTAACTGCTGGT      750

GGTATTGACACACACATCCACTTCATCTCCCCCCAACAAATCCCTACAGC      800

TTTTGCAAGCGGTGTAACAACGATGATTGGTGGCGGAACTGGCCCTGCTG      850

ATGGCACTAACGCAACCACTATCACTCCAGGCAGAAGAAATTTAAAATGG      900

ATGCTCAGAGCGGCTGAAGAATATTCTATGAATTTAGGTTTCTTAGCTAA      950

AGGTAACGCTTCTAATGATGCGAGCTTAGCCGATCAAATTGAAGCCGGTG      1000

CGATTGGCTTTAAAATCCATGAAGACTGGGGAACAACTCCTTCTGCAATC      1050

AATCATGCGTTAGATGTTGCGGACAAATACGATGTGCAAGTCGCTATCCA      1100

TACGGACACTTTGAATGAAGCCGGTTGTGTAGAAGACACTATGGCAGCCA      1150

TTGCCGGACGCACTATGCACACTTTCCACACTGAAGGCGCTGGTGGCGGA      1200

CACGCTCCTGATATCATTAAAGTAGCCGGCGAACACAACATTCTGCCCGC      1250

TTCCACTAACCCCACTATCCCTTTCACTGTGAATACAGAAGCAGAACACA      1300

TGGACATGCTTATGGTGTGCCACCACTTGGATAAAAGCATTAAAGAAGAT      1350

GTTCAGTTCGCTGATTCAAGGATCCGCCCTCAAACCATTGCGGCTGAAGA      1400

CACTTTGCATGACATGGGGATTTTCTCAATCACTAGTTCTGACTCTCAAG      1450

CTATGGGTCGTGTGGGTGAAGTTATCACCAGAACTTGGCAAACAGCTGAC      1500

AAAAACAAAAAAGAATTTGGCCGCTTGAAAGAAGAAAAAGGCGATAACGA      1550

CAACTTCAGAATCAAACGCTACTTGTCTAAATACACCATTAACCCAGCGA      1600

TCGCTCATGGGATTAGCGAGTATGTAGGTTCTGTAGAAGTGGGCAAAGTG      1650

GCTGACTTGGTATTGTGGAGTCCAGCATTCTTTGGCGTGAAACCCAACAT      1700

GATCATCAAAGGTGGGTTTATTGCATTGAGTCAAATGGGCGATGCGAACG      1750

CTTCTATCCCTACCCCACAACCAGTTTATTACAGAGAAATGTTCGCTCAT      1800

CATGGTAAAGCCAAATACGATGCAAACATCACTTTTGTGTCTAAAGCGGC      1850

TTATGACAAAGGCATTAAAGAAGAATTAGGGCTTGAAAGACAAGTGTTGC      1900

CGGTAAAAAATTGCAGAAACATCACTAAAAAAGACATGCAATTCAACGAC      1950

ACTACCGCTCACATTGAAGTCAATCCTGAAACTTACCATGTGTTCGTGGA      2000

TGGCAAAGAAGTAACTTCTAAACCAGCCACTAAAGTGAGCTTGGCGCAAC      2050

TCTTTAGCATTTTCTAA      2067
```

1.1.1.2 Construction of Expression Vector PET-28a-CTB-UreB:

Expression vector PET-28a and HP UreB-CTB fusion gene fragments were digested with NdeI and HindIII respectively. The DNA fragments of interest were recovered and purified from gels of agarose gel electrophoresis, followed by a ligation reaction. According to the principle that the molar ratio of the fragment of interest and the vector is 1:3 to 1:10, the ligation reaction was conducted at 16° C. for 16 hours. The ligation reaction system was designed as follows:

| | |
|---|---|
| DNA fragment of interest | 15 μl |
| PET-28a vector | 3 μl |
| Ligation buffer solution 10x | 2.5 μl |
| ddH$_2$O | 3.5 μl |
| T4 ligase | 1 μl |
| Total volume | 25 μl |

1.1.1.3 Preparation of Competent Cells of E. coli (CaCl$_2$ Method)

From −70° C. glycerol saved DH5a bacteria, a little bacteria was picked for streaking inoculation, A single colony of *E. coli* DH5a recipient strain was picked to be inoculated in a covered tube comprising 5 ml LB medium and cultured at 37° C. with shaking (200 rpm) for 10~42 hours to obtain a seed liquid. 5 ml of the seed liquid was inoculated in to 100 ml of fresh LB medium for culturing under shaking (200 rpm). When OD600 of the culture medium was 0.4~0.9, 1.5 ml of the culture medium was taken into an Eppendorf tube, placed on ice for 10 minutes and then centrifuged at 4° C. at 4000 rpm for 10 minutes, and the supernatant was carefully discarded. The first two steps were repeated once again to collect the cells. 300 μl of ice-cooled 0.1 mol/L CaCl$_2$ solution were added gently to re-suspend the cells, placed on ice for 30 minutes, centrifuged at 4000 rpm at 4° C. for 10 minutes, the supernatant was discarded, into the precipitate 100 μl of pre-cooled 0.1 mol/L CaCl$_2$ solution was added gently to suspend the cells, the competent cells were obtained. If the competent cells were needed to be stored for later use, pre-cooled 30 μl 50% glycerol and 70 μl of 0.1 mol/L of CaCl$_2$ solution (final concentration of 15% glycerol) were needed to re-suspend the cells, and saved the same at −70° C. (available for storage for six months) for later use.

1.1.1.4 the Ligation Products were Transformed into *E. coli* Competent Cells Competent cells suspension was taken from the −70° C. refrigerator and thawed at room temperature, after thawed it was placed on ice immediately. The ligation reaction solution (containing not more than 50 ng, the volume does not exceed 10 μl) was added therein, uniformly mixed by stirring lightly. The mixture was placed on ice for 30 minutes, in 42° C. water bath for 90 s for the thermal shock, then rapidly placed on ice to cool for 5 minutes, and then 800 μl LB liquid medium was added into the tube, mixed and cultured at 37° C., 150 rpm shaking culture for 1.5 hours. The resultant was spread on the screening plate containing kanamycin (Kan), and cultured at 37° C. overnight.

Figure 5:
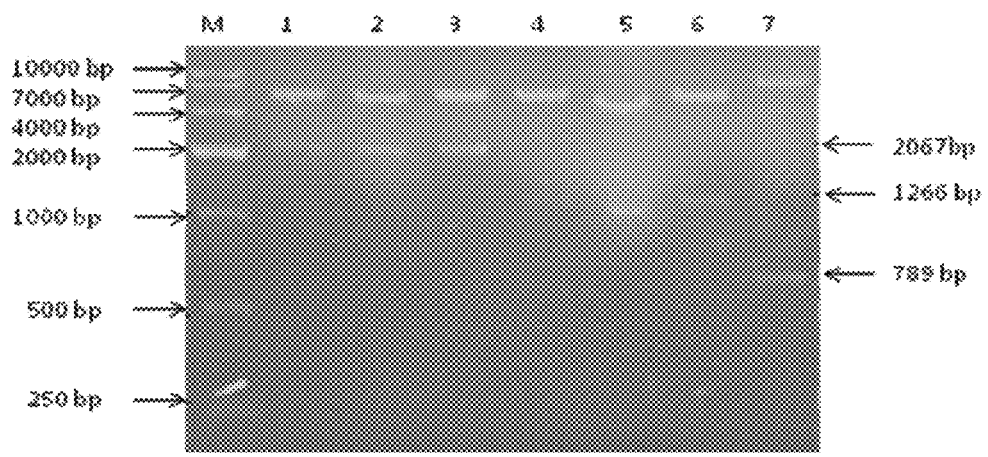
FIG. 5 is a photogram of electrophoresis results of double digestion of PET-28a-CTB-X plasmid according to an embodiment of the present invention, the samples for the respective lanes are as follows: M: DL 10000 DNA Marker; lanes 1, 2, 3: PET-28a-CTB-UreB double digestion; lanes 4, 5, 6: PET-28a-CTB-CagA double digestion; lane 7: PET-28a-CTB-NAP double digestion.

1.1.1.5 Construction of the Fusion Protein Colonies and Screening:

Single transformed DH5a colonies were picked to extract the plasmid therein. The fragment after double digestion showed a size of 2067 bp (see FIG. 5), which was consistent with the size of the design, confirmed the success of construction of the recombinant plasmid.

1.1.1.6 Construction and Screening of Fusion Protein Engineered Strain:

The methods for preparation of competent bacteria *E. coli* BL21-DE3 transformation, and plasmid extraction of recombinant bacteria were the same as that in the construction and screening of the bacteria for cloning.

Figure 6:
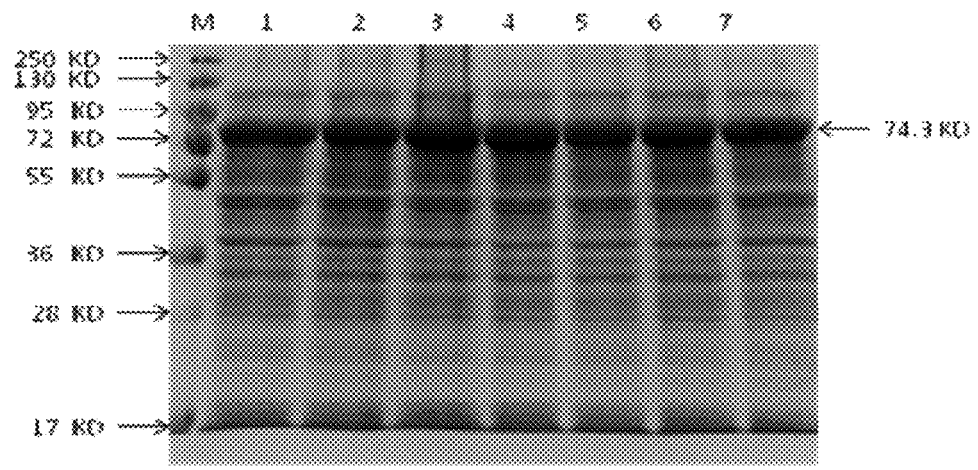
FIG. 6 is a photogram of protein electrophoresis results of the CTB-UreB fusion protein prepared according to an embodiment of the invention, the samples for the respective lanes are as follows: M: prestained Fermentas protein Marker; lanes 1, 2, 3, 4, 5, 6, and 7: the thallus of PET-28a-CTB-UreB/BL21-DE3 after induced with IPTG.

From the screening plates containing Kan single colonies were picked, and added to a test tube containing 5 ml LB, and cultured at 37° C., 150 rpm shaking for 4 hours. Then 1 mM IPTG was added for induction, the expression results are shown in FIG. 6.

1.1.2 Fermentation of the Recombinant Engineering Bacteria PET-28a-CTB-UreB/BL21 (DE3)

1.1.2.1 Seed Activation

The seed activation use the LB (tryptone 10 g/L; yeast extract 5 g/L; NaCl 10 g/L) medium and the volume thereof was 50 mL After 121° C. sterilization for 20 minutes, the medium was cooled and added with Kan (50 mg/L) and working seeds lot bacteria (each 500). The resultant was incubated at 37° C.±1° C. for 15 to 16 hours.

1.1.2.2 Preparation of Seeds

Before the 3 ml of the seeds' solution was added to the medium, the medium was sterilized at 121° C. for 20 minutes. The seeds was formulated to a volume of 3 L with 2YT medium (typtone 16 g/L, yeast extract 10 g/L, NaCl 5 g/L). The resultant were cultured at 37±1° C. for 4 to 6 hours.

1.1.2.3 Fermentation with Fermentor

1.1.2.3.1 Basal Medium

| | |
|---|---|
| Tryptone | 500 g |
| Yeast extrac | 250 g |
| (NH$_4$)$_2$SO$_4$ | 75 g |
| Glycerol | 250 g |
| MgSO$_4$•7H$_2$O | 50 g |
| KH$_2$PO$_4$ | 100 g |
| K$_2$HPO$_4$•3H$_2$O | 200 g |
| Na$_2$HPO$_4$•12H$_2$O | 350 g |

After dissolving the above basal medium with purified water, the resultant was added with purified water to 50 L.

1.1.2.3.2 Feed Supplement

| | |
|---|---|
| Glycerol | 2400 g |
| Tryptone | 600 g |
| Yeast extract | 600 g |
| MgSO$_4$•7H$_2$O | 24 g |

The feed supplement was formulated according to the above feeding formula. After dissolved with purified water, the resultant was added with purified water to 4 L, and 121° C. sterilized for 20 minutes before use.

1.1.2.3.3 Supplement of Alkali

1 L of 4M sodium hydroxide was prepared therein.

1.1.2.3.4 IPTG Solution 5.0 g IPTG was dissolved with sterile purified water, after 0.22 μm membrane filtration, the resultant was placed at 2 to 8° C. refrigerators for later use, with the storage period of 24 h.

1.1.2.3.5 Culture Parameters

Set culture parameters in the fermentor as the following:

| | |
|---|---|
| Culture temperature | 37° C. |
| Stirring speed | 200 rpm |

| | | |
|---|---|---|
| Alkali control | pH 7.0 | |
| Rota meter | 3 m³/h | |
| Vessel pressure | 0.03-0.05 Mpa | |
| dissolved oxygen | When the dissolved oxygen concentration is less than 30%, it is maintained as not less than 30% by increasing stirring speed and increasing the proportion of pure oxygen | |

Feed Supplement

| $OD_{600}$ | Rate for feeding carbon (ml/L * h) | Rate of feeding nitrogen (ml/L * h) |
|---|---|---|
| 4-5 | 5 | 5 |
| 9-11 | 10 | 10 |
| 20-25 | 12 | 12 |

When the $OD_{600}$ of the culture was between 20 and 30, IPTG solution was added, and the culture was continued for 3 hours and then the resultant was removed from the fermentor.

1.1.2.3.4 Centrifugation

In the end of the culture, the fermentation broth was transferred to a pre-cooled storage tank. After the fermentation broth is cooled to be below 15° C., the cells were harvested by centrifugation with the tube-type centrifuge.

1.1.3 Preparation of CTB-UreB/4CTB 1.1.3.1 Preparation of CTB-UreB (1) Preparation of Inclusion Body In the end of bacterial culture, the fermentation broth was transferred to a pre-cooled storage tank. After the fermentation broth is cooled to be below 15° C., the cells were harvested by centrifugation with the tube-type centrifuge.

The cells were re-suspended with a buffer of 50 mM Tris-HCl, 0.5% Triton X-100, 150 mM NaCl, 1 mM EDTA, pH 8.0 at a ratio of 1:10 (W/V). The suspension, after pre-cooled at 4° C., was homogenized under 900 bar high-pressure to break bacteria for 3 times. After centrifugation at 14000 g for 20 min, the precipitate was collected.

The collected inclusion bodies precipitate was washed at a ratio of 1:10 (W/V) with a buffer containing 50 mM Tris-HCl, 0.5% Triton X-100, 2M urea, 1 mM EDTA and pH 8.0 for three times, and a buffer containing 50 mM Tris-HCl, 5 mM DTT, pH8.0 for one time, respectively. Washing conditions: stirring at room temperature for 30 min, 6000 g centrifugation for 20 min.

(2) CTB-UreB Protein Denaturation

The inclusion bodies were dissolved with inclusion body dissolving solution containing 50 mM Tris-HCl, 8M urea, 10 mM DTT, 10% glycerol, pH8.0, stirred at 4° C. overnight, and centrifuged at 12000 rpm for 30 min, then the supernatant was collected for use.

(3) CTB-UreB Protein Purification

Purified CTB-UreB was obtained after DEAE and SPHP chromatography.

DEAE Column Purification

Equilibration buffer: 20 mM Tris-HCl, 8M urea, 10 mM DTT, 10% glycerol, pH8.0

Elution buffer: 20 mM Tris-HCl, 8M urea, 250 mM NaCl, 10 mM DTT, 10% glycerol, pH8.0

SPHP Purification

Equilibration buffer: 20 mM PB+8M urea+5 mM DTT+10% glycerol, pH7.2

Washing buffer: 20 mM PB, 8M urea, 30 mM NaCl, 5 mM DTT, 10% glycerol, pH7.2, conductivity of less than 3.7 ms/m Elution buffer: 20 mM PB, 8M urea, 0.3M NaCl, 5 mM DTT, 10% glycerol, pH7.2

Impurity washing buffer: 20 mM PB, 8M urea, 1M NaCl, 5 mM DTT, 10% glycerol, pH7.2

Figure 8:
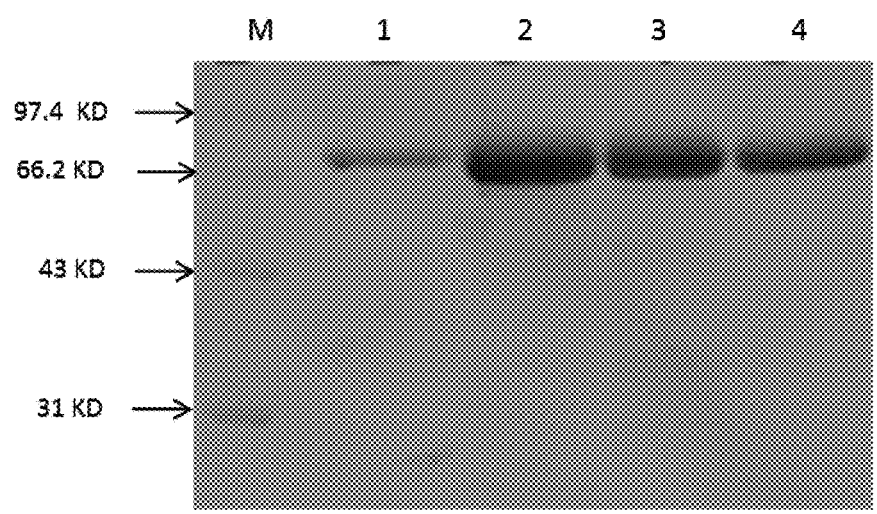
FIG. 8 is a photogram of protein electrophoresis results for purification of the CTB-UreB fusion protein prepared according to an embodiment of the invention, the samples for the respective lanes are as follows: M: prestained Fermentas protein Marker; lane 1: the sample collected before the eluted peak from SP HP peak; lanes 2 and 3: samples of eluted peak from the SP HP; lane 4: the sample collected after the eluted peak from the SP HP.

The photograph of electrophoresis for the purification of CTB-UreB is shown in FIG. 8.

1.1.3.2. Preparation of CTB-UreB/4CTB

The CTB bulk substance was diluted with a dilution buffer containing 50 mM Tris-HCl, 8M urea, pH8.0, and then the pH thereof was adjusted to pH 3.0 to 4.0. The resultant was incubated at room temperature for 1 hour and then the pH was adjusted to pH 8.0. The resultant was hold standby at 4° C.

The two proteins, CTB-UreB and CTB monomer, were mixed at a molar ratio of 1:4, and then were 5-fold volume diluted to a final refolding solution (50 mM Tris-HCl pH8.0+10% glycerol+150 mM NaCl). The concentration of DTT was controlled in the range of 0.2-1.0 mM, the concentration of urea was controlled in the range of 1.0M-2.5M. The resultant was allowed to stand overnight at room temperature.

The above solution was purified through chelating FF and QHP, and purified CTB-UreB/4CTB was obtained.

Chelating FF

Equilibration buffer: 20 mM Tris-HCl+5% glycerol+20 mM imidazole, pH8.0,

Elution buffer: 20 mM Tris-HCl+5% glycerol+200-300 mM imidazole for elution of the protein of interest, and the full peak was collected;

Impurity washing buffer: 20 mM Tris-HCl+5% glycerol+500 mM imidazole, pH8.0

QHP Purification

Buffer A: 20 mM Tris-HCl+5% glycerol, pH7.5

Buffer B: 20 mM Tris-HCl+5% glycerol+0.3M NaCl, pH7.5

0-100% B 10CV for elution of the protein of interest.

Figure 9A:
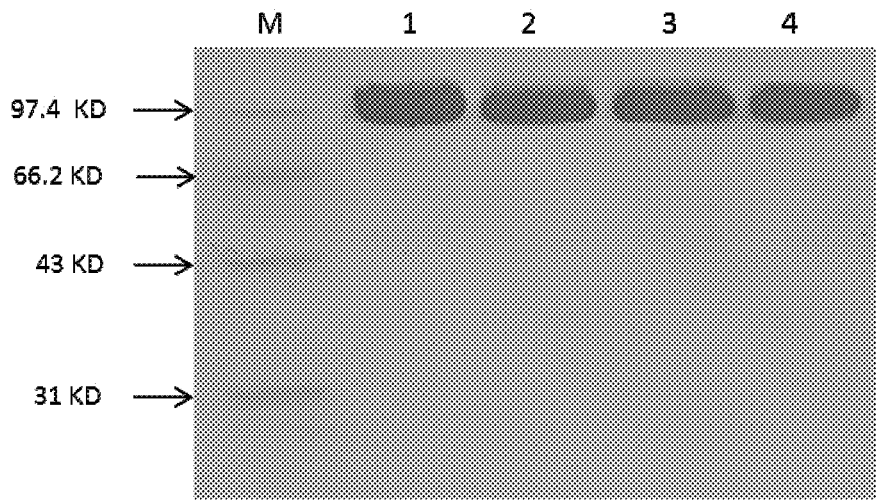
FIG. 9A is a photogram of protein electrophoresis results for purification of the CTB-UreB/4CTB chimeric protein prepared according to an embodiment of the invention, the samples for the respective lanes are as follows: M: prestained Fermentas protein Marker; lanes 1, 2, 3 and 4: eluted peak from QHP.

The results of electrophoresis for purification of CTB-UreB/4CTB are shown in FIG. 9A.

1.1.3.3. Study on the Stability

Figure 9B:
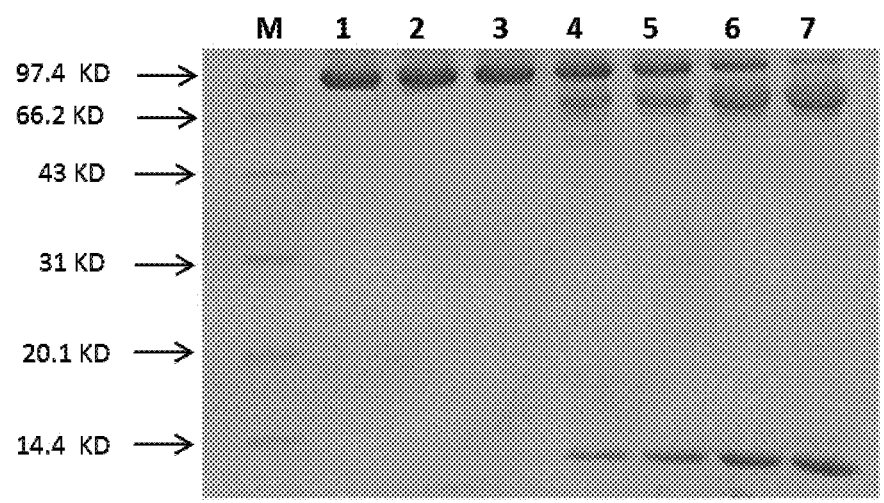
FIG. 9B is a photogram of protein electrophoresis results for stability test of the CTB-UreB/4CTB chimeric protein prepared according to an embodiment of the invention, the samples for the respective lanes are as follows: M: prestained Fermentas protein Marker; lanes 1 to 7 are the samples after treatment under the conditions of pH 9.0, 8.0, 7.0, 6.0, 5.0, 4.0, 3.0 respectively.

The pH in samples of purified CTB-UreB/4CTB chimera antigen bulk substance was adjusted to different value with hydrochloric acid. After standing for 1 hour at room temperature, the samples were taken for SDS-PAGE electrophoresis. The electrophoresis results are shown in FIG. 9B, in which samples of the various lanes are as follows: M: prestained Fermentas protein; lanes 1-7 are the samples after treatment under the conditions of pH 9.0, 8.0, 7.0, 6.0, 5.0, 4.0, 3.0 respectively.

It can be seen from the results of FIG. 9B, with the decrease of pH, the concentration of protein located at the chimera position was gradually reduced in the electrophoresis display, and a number of protein bands with molecular weight less than this chimera appeared, which suggests generation of the degradation products of smaller molecular weight. But the chimera protein at a pH higher than pH7.0, esp. pH8.0, was stable, and protein bands of smaller molecular weight than that of the chimeric protein did not appear. This shows that CTB-UreB/4CTB antigen chimera is stable at neutral to slightly alkaline environment, and under acidic environment is easily to be dissociated. Specifically, in the case of pH>7.0 it is relatively stable, preferably pH 8.0.

1.2 Preparation of CTB-CagA/4CTB

1.2.1 Construction of Recombinant Engineering Bacteria PET-28a-CTB-CagA/BL21-DE3

Figure 7:
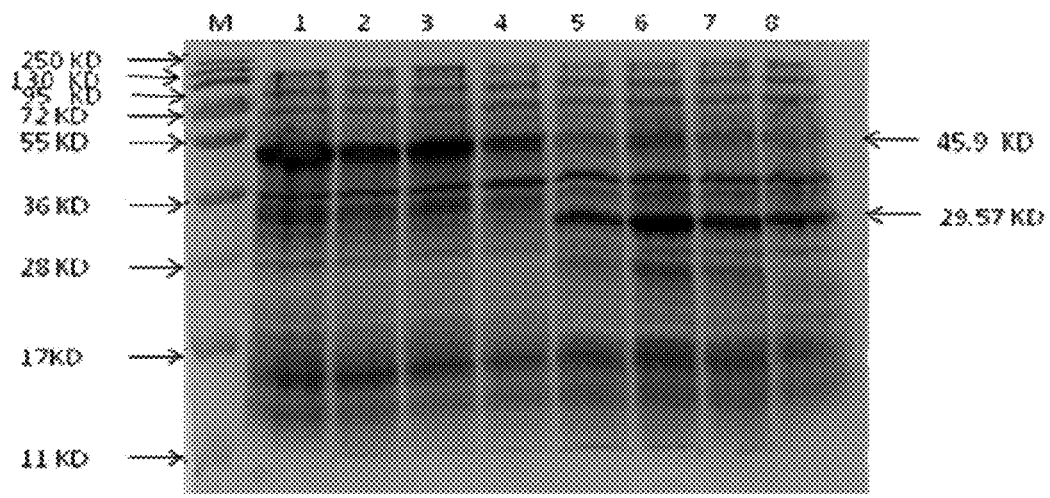
FIG. 7 is a photogram of protein electrophoresis results of the CTB-CagA fusion protein and CTB-NAP fusion protein prepared according to an embodiment of the invention, the samples for the respective lanes are as follows: M: prestained Fermentas protein Marker; lanes 1, 2, 3 and 4: the thallus of PET-28a-CTB-CagA/BL21-DE3 after induced with IPTG; lanes 5, 6, 7 and 8: the thallus of PET-28a-CTB-NAP/BL21-DE3 after induced with IPTG.

CTB-CagA was prepared by use of the same procedures as that in Example 1, except for that CagA gene was used instead of UreB gene. The size of the fragment of the constructed engineering strains plasmid after double-digested was 1266 bp (see FIG. 5), the expression of the fusion protein is shown in FIG. 7.

Gene sequence SEQ ID No.:2, wherein linker is shown in underlined and italics:

| | |
|---|---|
| ATGACACCTCAAAATATTACTGATTTGTGTGCAGAATACCACAACACACA | 50 |
| AATACATACGCTAAATGATAAGATATTTTCGTATACAGAATCTCTAGCTG | 100 |
| GAAAAAGAGAGATGGCTATCATTACTTTTAAGAATGGTGCAACTTTTCAA | 150 |
| GTAGAAGTACCAGGTAGTCAACATATAGATTCACAAAAAAAAGCGATTGA | 200 |
| AAGGATGAAGGATACCCTGAGGATTGCATATCTTACTGAAGCTAAAGTCG | 250 |
| AAAAGTTATGTGTATGGAATAATAAAACGCCTCATGCGATTGCCGCAATT | 300 |
| AGTATGGCAAAT*GGTGGTGGTGGTTCTGGTGGTGGTGGTTCTGGTGGTGG* | 350 |
| *TGGTTCT*ATGAAATTATTTGGAAATTCCAATAACAATAATAATGGACTCA | 400 |
| AAAACGAACCCATTTACGCTCAAGTTAATAAAAAGAAAGCAGGACAAGCA | 450 |
| ACTAGCCCTGAAGAGCCCATTTACGCTCAAGTTGCTAAAAAGGTGAGTGA | 500 |
| AAAAATTGACCAACTCAACGAAGCTACATCAGCAATAAATAGAAAAATTG | 550 |
| ACCGGATTAACAAAATTGCATCAGCAGGTAAAGGAGTGGGCGGTTTCAGT | 600 |
| GGAGCAGGGCGATCAGCTAGTCCTGAACCCATTTACGCTACAATTGATTT | 650 |
| TGATGAGGCAAATCAAGCAGGCTTCCCTCTTAGGAGAAGCACTGCAGTTA | 700 |
| ATGATCTCAGTAAAGTAGGGCTTTCAAGGGAACAAGAATTGACTCGTAGA | 750 |
| ATTGGCGATCTCAATCAGGCAGTGTCAGAAGCTAAAACAGGTCATTTTGA | 800 |
| CAAACTAGAACAAAAGATGGATGAACTCAAAGATTCTACAAAAAAGAATG | 850 |
| CTTTGAAGCTATGGGCTGAAAGCACGAAACAAGTGCCTACTGGTTTGCAG | 900 |
| GCGAAATTGGACAATTACGCTACTAACAGCCACACACGCATTAACAGTAA | 950 |
| TGTCCAAAATGGAGCAGTCAATGAGAAAGTGACCGGTATGCTAACGCAAA | 1000 |
| AAAACCCTGAGTGGCTCAAGCTCGTGAATGATAAGATAGTTGCACATAAT | 1050 |
| GTGGGAAGCGCTCATTTGTCAGAGTATGATAAAATTGGATTCAACCAAAA | 1100 |
| GAATATGAAAGATTATTCTGATTCGTTCAAGTTTTCCACCAAGTTGAACA | 1150 |
| ATGCCGTAAAAGACATTAAGTCTAGCTTTGTGCAATTTTTAACCAATACA | 1200 |
| TTTTCTACAGGATCTTACAGCTTGATGAAAGCAAATGCGGAACATGGAGT | 1250 |
| CAAAAATACTACAAAATAA | 1269 |

1.2.2 Fermentation of the Recombinant Engineering Bacteria PET-28a-CTB-CagA/BL21 (DE3)

The recombination engineering bacteria PET-28a-CTB-CagA/BL21 (DE3) was fermented in the same manner as that in Example 1.

1.2.3 Preparation of CTB-CagA/4CTB

1.2.3.1 Preparation of CTB-CagA (1) The CTB-CagA inclusion bodies were extracted with the same method as that in Example 1.

(2) The inclusion bodies were mixed with a inclusion body dissolving solution at a ratio of 1:20 (W/V), stirred at 4° C. for 3 hours, standing overnight, the supernatant was collected by 12000 rpm centrifugation for 30 min.

(3) Q FF column purification
Buffer A: 20 mM Tris-HCl+8M urea+5 mM DTT+5% Glycerol, pH7.5
Buffer B: 20 mM Tris-HCl, 8M urea, 1.0M NaCl, 5 mMDTT, 5% glycerol, pH7.5
The column was balanced and rinsed with Buffer A and eluted with Buffer B.

(4) SP Big beads purification
Buffer A: 20 mM Tris-HCl, 8M urea, 5 mM DTT, 5% glycerol, pH7.5
Buffer B: 20 mM Tris-HCl, 8M urea, 150 mM NaCl, 5 mM DTT, 5% glycerol, pH7.5
The column was balanced and rinsed with Buffer A and eluted with Buffer B.

Figure 10:
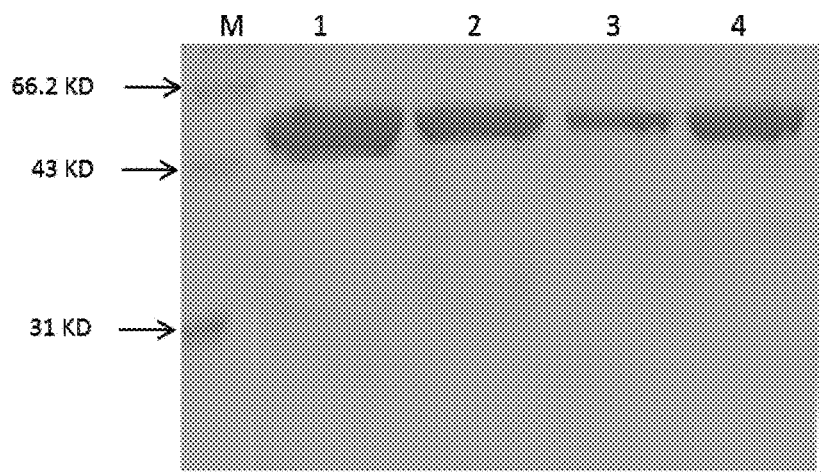
FIG. 10 is a photogram of protein electrophoresis results for purification of the CTB-CagA fusion protein prepared according to an embodiment of the invention, the samples for the respective lanes are as follows: M: prestained Fermentas protein Marker; lanes 1, 2, 3 and 4: eluted peak from QHP.

The electrophoresis photograph for CTB-CagA purification is shown in FIG. 10.

1.2.3.2 Preparation of CTB-CagA/4CTB

The CTB bulk substance was diluted with a dilution buffer containing 50 mM Tris-HCl, 8M urea, pH8.0, and then the pH thereof was adjusted to pH 3.0 to 4.0. The resultant was incubated at room temperature for 1 hour and then the pH was adjusted to pH 8.0. The resultant was hold standby at 4° C.

The two proteins, CTB-CagA and CTB monomer, were mixed at a molar ratio of 1:4, and then were 5-fold volume diluted to a final refolding solution (50 mM Tris-HCl pH8.0+10% glycerol+150 mM NaCl). The concentration of DTT was controlled in the range of 0.2-1.0 mM, the concentration of urea was controlled in the range of 1.0M-2.5M. The resultant was allowed to stand overnight at room temperature.

The above solution was purified through chelating FF and SP HP, and purified CTB-CagA/4CTB was obtained.
Chelating FF Column Purification
Buffer A: 20 mM Tris-HCl+5% glycerol+20 mM imidazole, pH8.0
Buffer B: 20 mM Tris-HCl+5% glycerol+200 mM imidazole, for elution of the protein of interest
Impurity was washed with 100% Buffer B.
SP HP Column Purification
Buffer A: 20 mM Tris-HCl+5% glycerol, pH7.5
Buffer B: 20 mM Tris-HCl+5% glycerol+0.3M NaCl, pH7.5

Figure 11A:
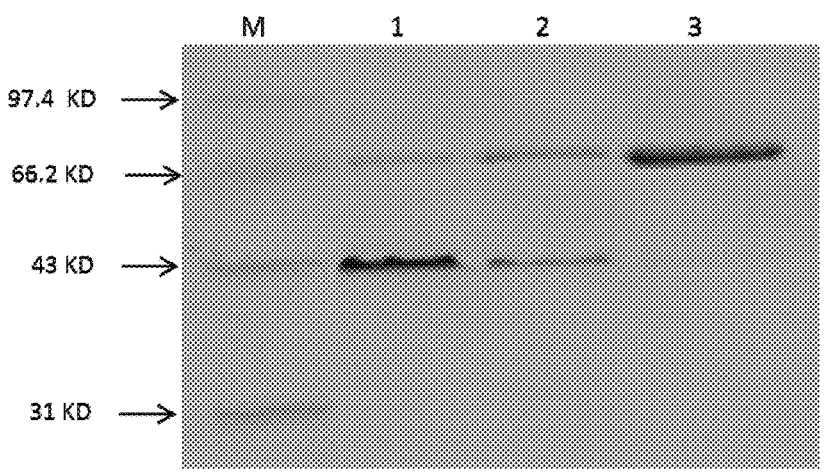
FIG. 11A is a photogram of protein electrophoresis results for purification of the CTB-CagA/4CTB chimeric protein prepared according to an embodiment of the invention, the samples for the respective lanes are as follows: M: prestained Fermentas protein Marker; lanes 1, 2 and 3: eluted peak from SP HP.

The electrophoresis photographs for purification of CTB-CagA/4CTB chimeric protein are shown in FIG. 11A.

1.2.3.3 Study on Stability

Figure 11B:
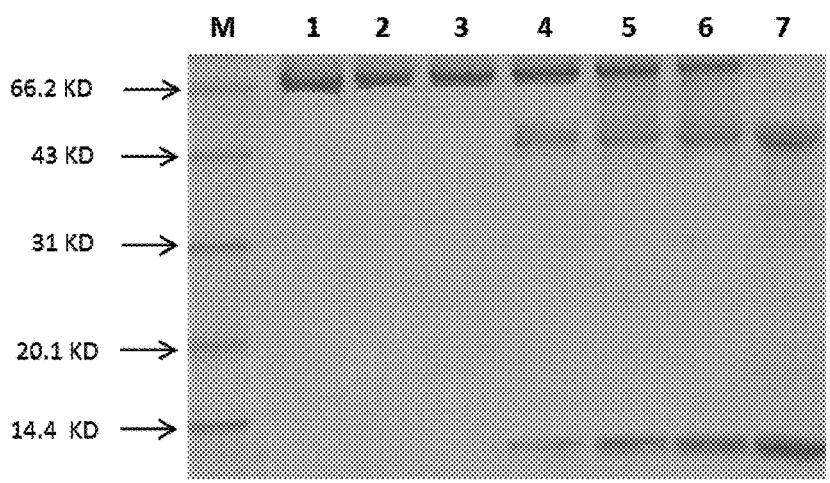
FIG. 11B is a photogram of protein electrophoresis results for stability test of the CTB-CagA/4CTB chimeric protein prepared according to an embodiment of the invention, the samples for the respective lanes are as follows: M: prestained Fermentas protein Marker; lanes 1 to 7: are the samples after treatment under the conditions of pH 9.0, 8.0, 7.0, 6.0, 5.0, 4.0, 3.0 respectively.

The pH in samples of purified CTB-CagA/4CTB chimera antigen bulk substance was adjusted to different value by being diluted with hydrochloric acid. After standing for 1 hour at room temperature, the samples were taken for SDS-PAGE electrophoresis. The electrophoresis results are shown in FIG. 11B, in which samples of the various lanes are as follows: M: prestained Fermentas protein; lanes 1-7 are the samples after treatment under the conditions of pH 9.0, 8.0, 7.0, 6.0, 5.0, 4.0, 3.0 respectively.

It can be seen from the results of FIG. 11B, with the decrease of pH the concentration of protein located at the chimera position was gradually reduced in the electrophoresis display, and a number of protein bands with molecular weight less than this chimera appeared, which suggests generation of the degradation products of smaller molecular weight. But the chimera protein at a pH higher than pH7.0, esp. pH8.0, was stable, and protein bands of smaller molecular weight than that of the chimeric protein did not appear. This shows that CTB-CagA/4CTB antigen chimera is stable at neutral to slightly alkaline environment, and under acidic environment is easily to be dissociated. Specifically, in the case of pH>7.0 it is relatively stable, preferably pH 8.0.

1.3 Preparation of CTB-NAP/4CTB 1.3.1 Construction of Recombinant Engineering Bacteria Pet-28a-CTB-NAP/BL21-DE3

CTB-NAP was prepared by use of the same procedures as that in Example 1, except for that NAP gene was used instead of UreB gene. The size of the fragment of the constructed engineering strains plasmid after double-digested was 789 bp (see FIG. 5), the expression of the fusion protein is shown in FIG. 7.

Gene sequence SEQ ID No.:3, wherein the linker is shown in underlined and italics:

```
ATGACACCTCAAAATATTACTGATTTGTGTGCAGAATACCACAACACACA      50

AATACATACGCTAAATGATAAGATATTTTCGTATACAGAATCTCTAGCTG     100

GAAAAGAGAGATGGCTATCATTACTTTTAAGAATGGTGCAACTTTTCAA      150

GTAGAAGTACCAGGTAGTCAACATATAGATTCACAAAAAAAAGCGATTGA    200

AAGGATGAAGGATACCCTGAGGATTGCATATCTTACTGAAGCTAAAGTCG    250

AAAAGTTATGTGTATGGAATAATAAAACGCCTCATGCGATTGCCGCAATT    300

AGTATGGCAAAT<u>*GGTGGTGGTGGTTCTGGTGGTGGTGGTTCTGGTGGTGG*</u>  350

<u>*TGGTTCT*</u>ATGAAAACATTTGAAATTTTAAAACATTTGCAAGCGGATGCGA   400

TCGTGTTGTTTATGAAAGTGCATAACTTCCATTGGAATGTGAAAGGCACG    450

GATTTTTTTAATGTACATAAAGCTACTGAAGAAATTTATGAAGAGTTTGC    500

GGACATGTTTGATGATCTCGCTGAAAGGATCGTTCAATTAGGACACCACC    550

CCTTAGTCACTTTATCCGAAGCGATCAAACTCACTCGTGTTAAAGAAGAA    600

ACTAAAACGAGCTTCCACTCTAAAGACATTTTTAAAGAAATTCTAGAGGA    650

CTATAAACACCTAGAAAAAGAATTTAAAGAGCTCTCTAACACCGCTGAAA    700

AAGAAGGCGATAAAGTCACCGTAACTTATGCGGATGATCAATTGGCCAAG   750

TTGCAAAAATCCATTTGGATGCTGCAAGCCCATTTAGCTTAA            792
```

1.3.2 Fermentation of the Recombinant Engineering Bacteria PET-28a-CTB-NAP/BL21 (DE3)

The recombination engineering bacteria PET-28a-CTB-NAP/BL21 (DE3) was fermented in the same manner as that in Example 1.

1.3.3 Preparation of CTB-NAP/4CTB 1.3.3.1 Preparation of CTB-NAP (1) The CTB-NAP inclusion bodies were extracted with the same method as that in Example 1.

(2) The CTB-NAP inclusion bodies were dissolved with a pH8.0 buffer containing 20 mM Tris-HCl, 8M urea, incubated overnight, and then the supernatant was collected by 12000 rpm centrifugation for 30 min.

(3) QFF chromatography:

Buffer A: 20 mM Tris-HCl+5% glycerol, pH7.5

Buffer B: 20 mM Tris-HCl+5% glycerol+0.3M NaCl, pH7.5

Figure 12:
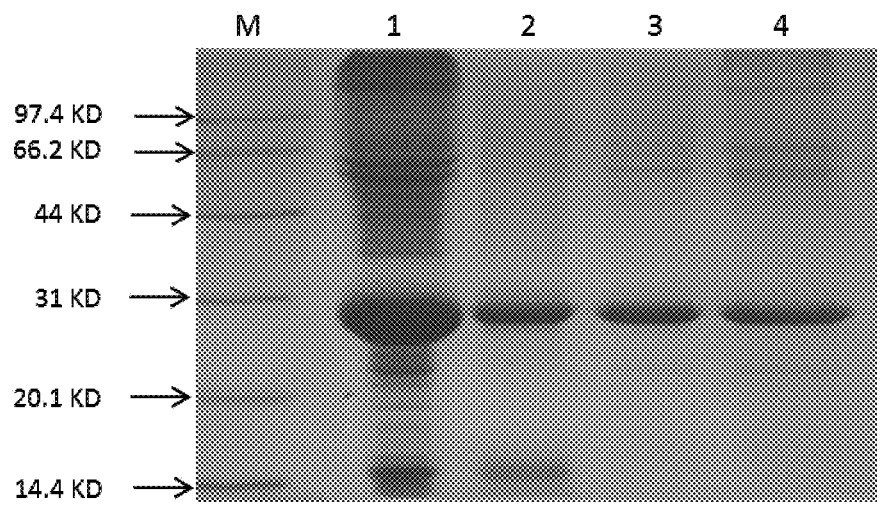
FIG. 12 is a photogram of protein electrophoresis results for purification of the CTB-NAP fusion protein prepared according to an embodiment of the invention, the samples for the respective lanes are as follows: M: prestained Fermentas protein Marker; lane 1: inclusion body (in 8M Urea); lanes 2, 3 and 4: eluted peak from QHP.

The column was balanced and rinsed with Buffer A and eluted with Buffer B. The photograph of electrophoresis for purification of CTB-NAP fusion protein is shown in FIG. 12.

1.3.3.2 Preparation of CTB-NAP/4CTB (1) Processing of CTB-NAP: the CTB-NAP sample was diluted with a pH8.0 buffer containing 20 mM Tris-HCl, 8M urea, and then the pH thereof was adjusted to pH 8.0. Then Mercaptoethanol was added to a final concentration of 3 mM.

(2) Processing of CTB: The CTB bulk substance was diluted with a pH8.0 dilution buffer containing 20 mM Tris-HCl, 8M urea, and then the pH thereof was adjusted to pH 3.5 to 3.7. The resultant was incubated at room temperature for 1 hour and then the pH was adjusted to pH 8.0. Mercaptoethanol was added to a final concentration of 3 mM.

(3) Renaturation:

The two processed proteins CTB-NAP and CTB monomer were mixed at a molar ratio of 1:4, and then were diluted at a ratio of 1:6 with a pH8.0 buffer of 50 mM Tris-HCl, 5% glycerol, 0.03 mM GSSG. The concentration of mercaptoethanol was controlled in the range of 0.2-1.0 mM, the concentration of urea was controlled in the range of 1.0M-2.5M. The resultant was allowed to stand overnight at 21° C.

(4) NI FF purification:

Buffer A: 50 mM Tris-HCl+5% glycerol+20 mM imidazole, pH8.0

Buffer B: 50 mM Tris-HCl+5% glycerol+300 mM imidazole, pH8.0

Imidazole was added to the sample for renaturation to a final concentration of 20 mM. The sample was loaded on NI FF column, the flow rate was 8 ml/min, and the column was rinsed with Buffer A and eluted with Buffer B.

(5) QHP purification

Buffer A: 50 mM Tris-HCl+5% glycerol,

Buffer B: 50 mM Tris-HCl+5% glycerol+1M NaCl, pH8.0

The eluted sample of NI FF column (with conductivity between 4 and 5) was loaded on QHP column with a flow rate of 3 ml/min. Then column was balanced and rinsed with Buffer A and eluted with 30% of Buffer B in a flow rate of 1 ml/min.

Figure 13:
FIG. 13 is a photogram of protein electrophoresis results for purification of the CTB-NAP/4CTB chimeric protein prepared according to an embodiment of the invention, the samples for the respective lanes are as follows: M: prestained Fermentas protein Marker; lanes 1, 2 and 3: eluted peak from QHP.

The electrophoresis photographs for purification of CTB-NAP/4CTB chimeric protein are shown in FIG. 13.

2. Study on the Immunogenicity of Recombinant *H. pylori* (rHP) Vaccine on Mice 2.1 Study on the Immunogenicity of the Chimera Protein CTB-UreB/4CTB 2.1.1 Immunization Method for BALB/c Mice 2.1.1.1 Test System: 8-10 Weeks Old, Weighting 18-20 g, SPF Grade Female BALB/c Mice.

2.1.1.2 Test Articles:

UreB, CTB-UreB fusion protein, CTB-UreB/4CTB chimeric proteins, were respectively diluted with Tris-HCl buffer (pH 8.0). The dose for UreB protein immunization is 20 μg/mouse, CTB-UreB fusion proteins and CTB-UreB/4CTB chimeric proteins are administered with equivalent molar amount with that of UreB in UreB protein group. The antacids were diluted with PBS to 50 mg/ml.

2.1.1.3 the 4 Groups were Set in this Study:

UreB group, CTB-UreB group, CTB-UreB/4CTB group and saline group (or named blank control group (CON, Control)).

2.1.1.4 Immunization Program for Mice:

the mice were immunized for a total of four times each with intervals of 7 days therebetween. Each animal was orally administered with 0.2 ml of the experimental medicines via gavage. 10 minutes prior to the administration 0.2 ml antacids was administered. All animals fasted 12 h except water prior to the administration. Water and food were fed again one hour after administration.

2.1.1.5 Samples Collection and Testing:

Blood of each group of mice were collected in one day before the immunization and 2 weeks, 4 weeks, 6 weeks, 8 weeks, 10 weeks after the first immunization, for measurement of serum IgG and IgA antibody levels. With exception for that the last collection was obtained via eyeball; other collections of blood are obtained from tails of the mice. All the blood samples were placed at 4° C. overnight, the next day all the samples were centrifuged at 4° C., 5000 rpm for 15 min, the supernatant of serum was taken, −20° C. to preserve.

All the animals were sacrificed after blood collection via eyeball 10 weeks after first immunization. After laparotomy, 10 cm ileum near the end of the ileocecal was cut and washed with PBS for three times, the intestinal mucosa was scraped with sterile blade to be dissolved in 1 ml 0.01 mol/L PBS buffer (pH7.4, containing 50 mmol/L EDTA, 20 nmol/L protease inhibitors leupeptin and pepstatin). The resultant was centrifuged at 10000 rpm for 10 min, the supernatant was taken and 20 μl of 100 mmol/L PMSF (Sigma) was added therein. Levels of serum IgG and intestinal mucosa sIgA antibodies were measured with ELISA. In 96 well microtiter plate each well was added with 100 μl UreB antigen (1.25 μg/ml), coating at 4° C. overnight. Solutions in the well were discard next day and the wells was washed three times with PBST; each well was added of blocking solution 200 μl (containing 2% BSA), 37° C. blocking 2 h, and washed with PBST 3 times; 100 μl serum (1:300 dilution) was added to each well, the wells were washed with PBST three times after reaction at 37° C. for 1 hour, each well was added with 100 μl HRP labeled goat anti-mouse IgG (1:2000-1:50000)/HRP labeled goat anti-mouse IgA (1:4000-1:8000), inoculated at 37° C. for 1 hour, and then washed with PBST for 6 times; freshly prepared substrate solution was immediately added per well 100 μl, leave for reaction at room temperature for 15 min, stop solution 50 μl was added therein; Absorbance OD 450 value of each well were measured with microplate detector.

2.1.2 Results

Figure 14:
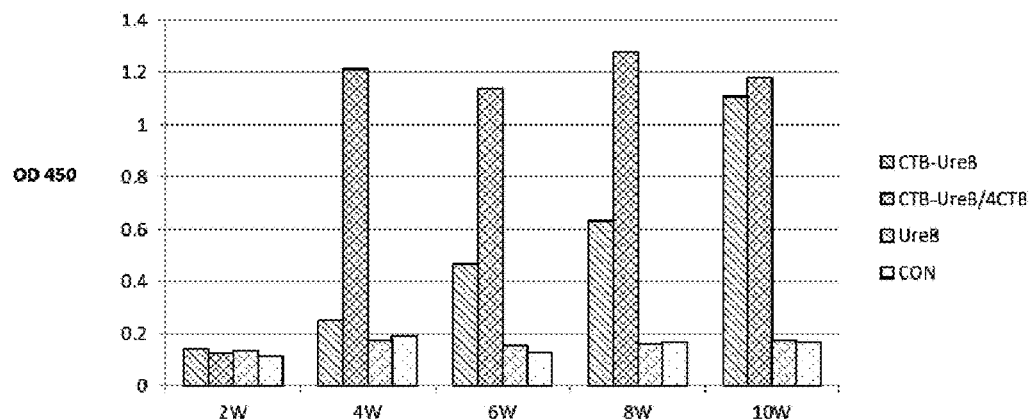
FIG. 14 shows the measurement results of serum specific IgG obtained by immunizing mice with CTB-UreB/4CTB chimeric protein according to an embodiment of the invention.
Figure 15:
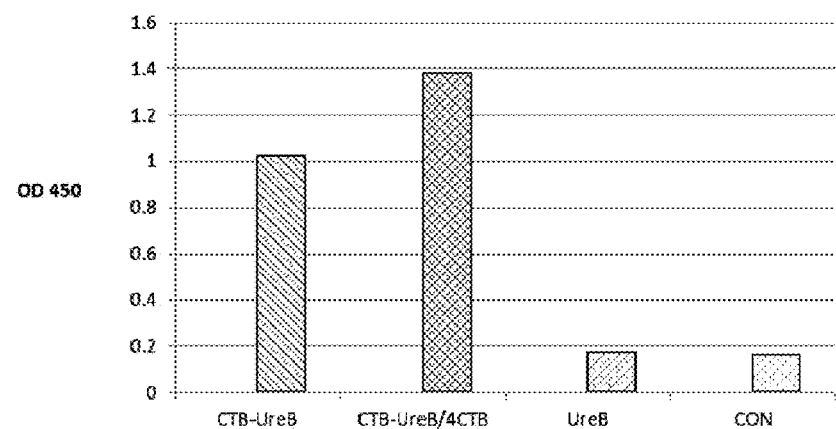
FIG. 15 shows the measurement results of intestinal mucosa specific sIgA obtained by immunizing mice with CTB-UreB/4CTB chimeric protein according to an embodiment of the invention.

Serum IgG and intestinal mucosal antibody sIgA response of BALB/C mice after HP vaccine oral immunization, were shown in FIGS. 14 and 15. Antibodies level of mice in the control group and UreB protein group did not increase after the administration, on the contrary, serum IgG antibody level of the mice in CTB-UreB fusion protein group and CTB-UreB/4CTB chimeric protein group was significantly increased 4 weeks after the first immunization and reached the peak in 8 weeks, the comparison showed that there were significant differences (P<0.001) as compared with the control group for both groups; levels of sIgA intestinal mucosal antibody for these two groups were obviously increased and the comparison with control group showed significant differences (P<0.001). Wherein for the anti-UreB antibody in mice of the fusion protein CTB-UreB group, seroconversion rate was 60%; for anti-UreB antibody in mice of the CTB-UreB/4CTB chimeric protein group, seroconversion rate was 95%, indicating that CTB-UreB/4CTB chimera protein vaccine can induce a significant immune response.

2.1.3 Conclusion

Oral administration of recombinant CTB-UreB fusion protein and CTB-UreB/4CTB chimera protein can stimulate the body to produce specific antibodies against UreB antigen. However, the immune response caused by CTB-UreB/4CTB chimera protein was significantly better than that of CTB-UreB fusion protein, indicating that CTB-UreB/4CTB chimeric protein has a better immune response and immunogenicity, and thus can be used as a candidate for the prevention vaccine of H. pylori.

2.2 Immunogenicity of CTB-CagA/4CTB Chimera Protein

2.2.1 Immunization Method for BALB/c Mice

Figure 16:
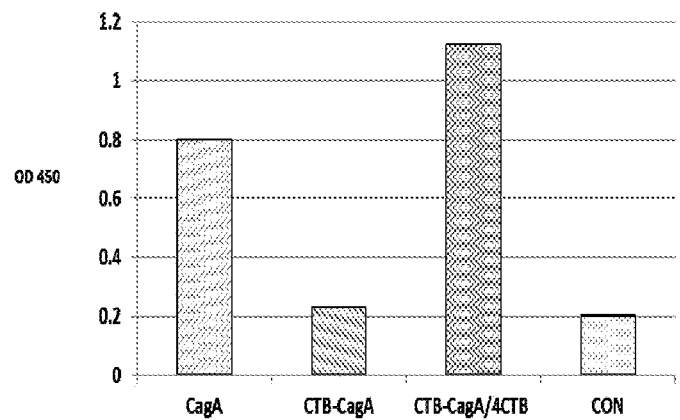
FIG. 16 shows the measurement results of serum specific IgG obtained by immunizing mice with CTB-CagA/4CTB chimeric protein according to an embodiment of the invention.
Figure 17:
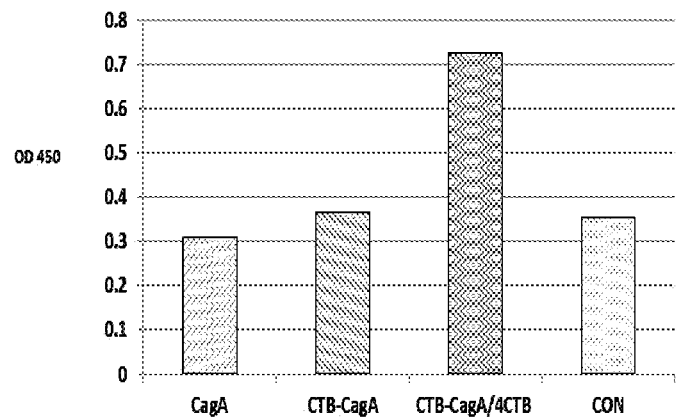
FIG. 17 shows the measurement results of intestinal mucosa specific sIgA obtained by immunizing mice with CTB-CagA/4CTB chimeric protein according to an embodiment of the invention.

The immunization method was the same as that described in section 2.1.1. Wherein, Cag A protein, CTB-CagA fusion protein, CTB-CagA/4CTB chimeric proteins were respectively diluted with Tris-HCl buffer (pH 8.0). The dose for CagA protein immunization is 200 µg/mouse, CTB-CagA fusion proteins and CTB-CagA/4CTB chimeric proteins are administered with equivalent molar amount with that of CagA in CagA protein group and in a volume of 0.2 ml/mouse. In ELISA the wells were coated with CagA antigen. The response of serum IgG and intestinal mucosal sIgA antibody were shown in FIGS. 16 and 17.

2.2.2 Conclusion

Oral administration of recombinant CTB-CagA/4CTB chimeric protein can stimulate the body to produce specific anti-CagA antigen antibodies. The results indicate that CTB-CagA/4CTB chimeric protein has a better immune response and immunogenicity, and thus can be used as a vaccine candidate for prevention of Helicobacter pylori.

2.3 Immunogenicity of CTB-NAP/4CTB Chimera Protein

2.3.1 Immunization Method for BALB/c Mice

The immunization method was the same as that described in section 2.1.1. Wherein the test articles NAP protein, CTB-NAP fusion protein, CTB-NAP 4CTB chimeric proteins were respectively diluted with Tris-HCl buffer (pH 8.0). The dose for NAP protein immunization is 200 µg/mouse, CTB-NAP fusion protein and CTB-NAP/4CTB chimeric proteins are administered with equivalent molar amount with that of NAP in NAP protein group and the volume thereof was 0.2 ml/mouse. In ELISA the wells were blocked with NAP antigen.

2.3.2 Results

Figure 18:
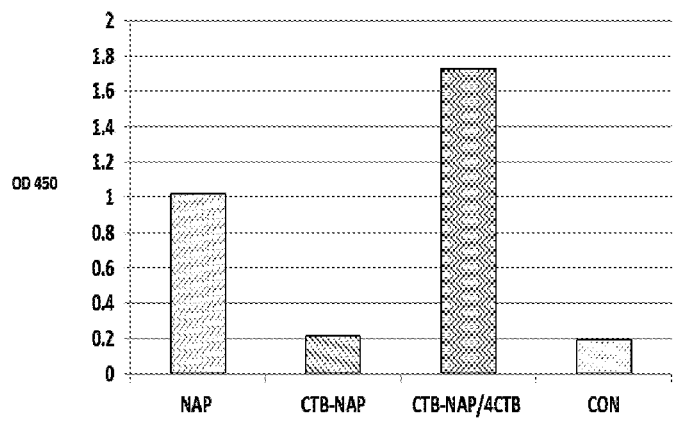
FIG. 18 shows the measurement results of serum specific IgG obtained by immunizing mice with CTB-NAP/4CTB chimeric protein according to an embodiment of the invention.
Figure 19:
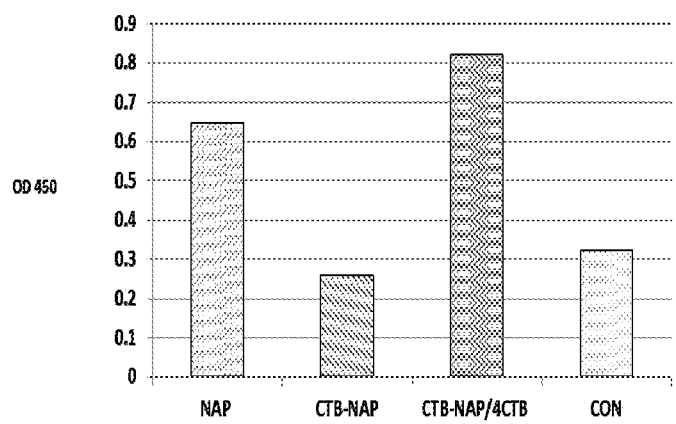
FIG. 19 shows the measurement results of intestinal mucosa specific sIgA obtained by immunizing mice with CTB-NAP/4CTB chimeric protein according to an embodiment of the invention.

After immunized with the HP vaccine, the response of serum IgG and intestinal mucosal sIgA antibody in BALB/c mice were shown in FIGS. 18 and 19.

2.3.3 Conclusion

Oral administration of recombinant CTB-NAP/4CTB chimeric protein can stimulate the body to produce specific anti-NAP antigen antibodies. The results indicate that CTB-NAP/4CTB chimeric protein has a better immune response and immunogenicity, and thus can be used as a vaccine candidate for prevention of Helicobacter pylori.

3. The Immune Protection of Recombinant H. pylori Vaccine Against H. pylori SS1 Strain Infection in BALB/c Mice

3.1 Test Method 3.1.1 the Immunization Method was the Same as that of Section 2.1.1.

3.1.2 HP SS1 Bacteria Challenge:

Two weeks after the last immunization, animals of test group and negative control group were oral administered via gavage 0.2 ml ($1 \times 10^9$ CFU/ml) of HP SS1 bacteria once per day for consecutive three days. 0.2 ml antacids were oral administrated via gavage at 10 min before the administration of HP SS1 bacteria.

3.1.3 Sample Collection and Testing

Sample collection and testing methods for serum and intestinal mucosa were the same as that in section 2.1.1.5.

All animals were sacrificed four weeks after challenged with HPSS1 bacteria, stomach thereof were taken out after laparotomy, divided along the longitudinal axis the stomach tissue into three sections, each section includes the three parts of fundus, gastric body and antrum. One section was used to do a quantitative culture of bacteria therein: antrum tissue was gripped with sterile tweezers, the submucosal surface thereof was used to coat selective HP culture plate, at 37° C., and then the plate was cultured under microaerobic conditions for about 1 day. If transparent, smooth, small needle-like colonies could be seen, it was deemed as a positive sample.

Second section was used for rapid urease test in a 96-well plate: the urease reagent solution was added to each well of the 96-well plates containing rat stomach tissue, each well was quantitated to 100 µl, and stood closed at room temperature for 0.5 hour. If the color of the reagent is changed from yellow to red, it is deemed as a positive sample, i.e. the sample had Hp infection.

The third section was fixed at 4% paraformaldehyde, paraffin-embedded, sliced, HE staining, Giemsa staining, and the HP SSI bacteria colonization and inflammatory tissue was observed with a microscope.

3.2 Results 3.2.1 Observation of the Toxicity and Adverse Effects in Mice after Immunization/Challenge Each group of mice were in good mental state, no listlessness, diarrhea and other adverse effects were seen.

3.2.2 Serum/Intestinal Mucosa IgG/sIgA Antibody Results

Figure 20:
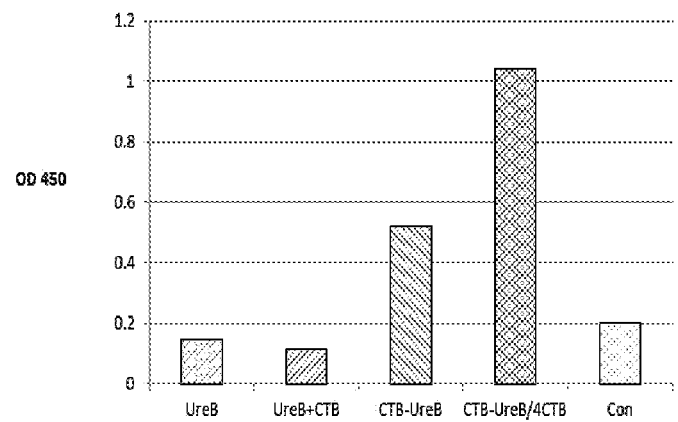
FIG. 20 shows the measurement results of serum specific IgG antibodies obtained by immunizing mice with CTB-UreB/4CTB chimeric protein according to an embodiment of the invention and then challenging the immunized mice with HPSS1.
Figure 21:
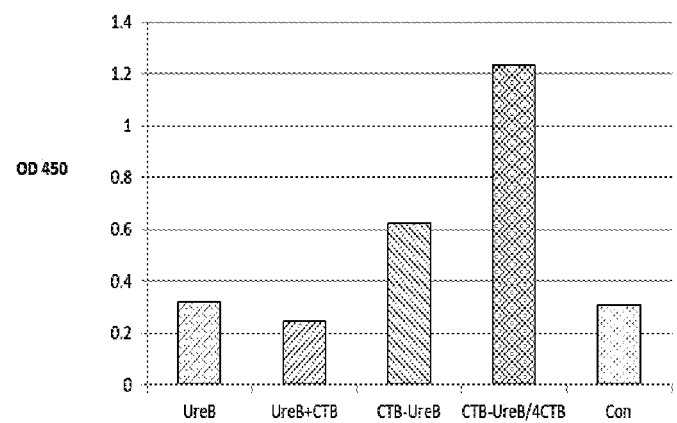
FIG. 21 shows the measurement results of intestinal mucosa specific sIgA antibodies obtained by immunizing mice with CTB-UreB/4CTB chimeric protein according to an embodiment of the invention and then challenging the immunized mice with HPSS1.

Antibodies of blank control group, UreB protein group and UreB+CTB group mice did not increase after administration, while in CTB-UreB fusion protein group mice and CTB-UreB/4CTB chimeric protein group mice serum IgG antibodies and intestinal mucosal antibody sIgA increased significantly in 9.5 weeks after the first administration, and the comparison with the blank control group showed significant difference. The results are shown in FIGS. 20 and 21.

3.2.3 Tissue Smears and Rapid Detection of Urease

Each group of mice were tested with rapid urease test and tissue smear four weeks after the challenge, the results thereof showed: all the eight animals of the model group were infected with HPSS1, both urease test and tissue smears showed positive results; for all animals of the Blank control group (not given HPSS challenge), urease test and tissue smears showed negative results; seven animals in UreB group showed positive results of urease test and tissue smear test; five animals in CTB-UreB group showed urease positive results, wherein four animals smear result is positive; only one animal in CTB-UreB/4CTB group showed positive result for a urease test, and all the animals in CTB-UreB/4CTB group showed negative smear results. The results are shown in Table 1.

TABLE 1

Test results of mice orally administered with rHP vaccine according to the embodiment of the present invention, followed by the challenge of HPSS1

| Group | Number of animals (n) | Positive rate of HP test (%) | | | Protection rate (%) |
|---|---|---|---|---|---|
| | | Rapid urease test | Tissue smear | Tissue section | |
| UreB | 8 | 87.5 (7/8) | 87.5 (7/8) | 87.5 (7/8) | 12.5 |
| CTB-UreB | 8 | 62.5 (5/8) | 50 (4/8) | 62.5 (5/8) | 37.5 |
| CTB-UreB/4CTB | 8 | 12.5 (1/8) | 0 (0/8) | 12.5 (1/8) | 87.5 |
| Model control (positive control) | 8 | 100 (8/8) | 100 (8/8) | 100 (8/8) | 0 |
| Blank control (negative control) | 8 | 0 (0/8) | 0 (0/8) | 0 (0/8) | — |

3.2.4 Results of Histopathology Staining

Figure 22A:
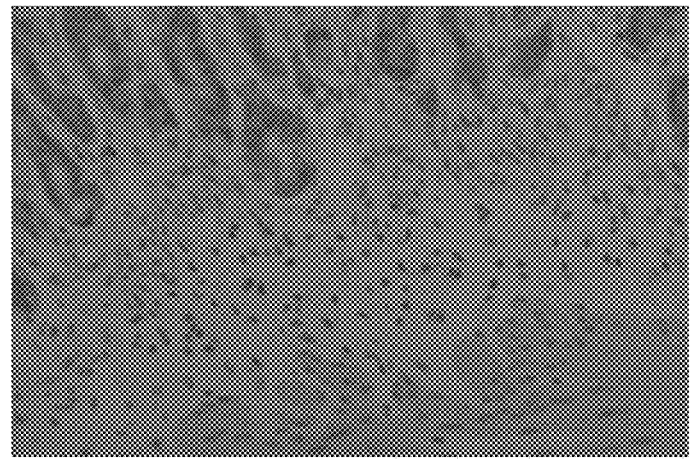
FIG. 22 shows the results of pathological sections for gastric tissue of the mice which were immunized with CTB-UreB/4CTB chimeric protein according to an embodiment of the invention and then challenged with HPSS1, wherein, A: representative pathological section for gastric tissue of the mice in CTB-UreB/4CTB chimeric protein group (×250); B: representative pathological section for gastric tissue of the mice in UreB group (×250); C: representative pathological section for gastric tissue of the mice in UreB group (×400)
Figure 22B:
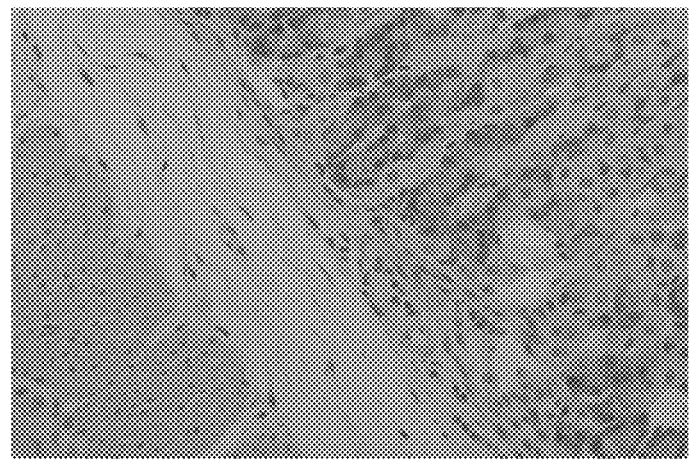
Figure 22C:
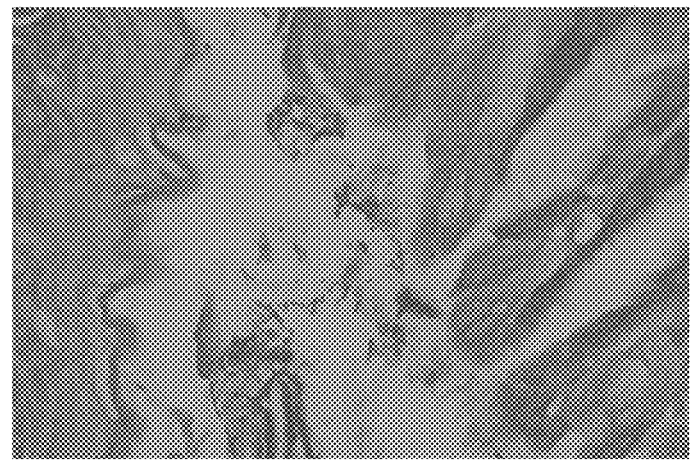

Mice of the control group showed in the gastric pits thereof many conglobate *H. pylori* colonization, a large number of macrophages and neutrophils infiltration in deep to the middle of gastric mucosal lamina propria. Mice of the CTB-UreB fusion protein group showed a small amount of *Helicobacter pylori* colonization in the gastric pits, moderate macrophage and neutrophil infiltration and mild inflammation in deep of gastric mucosal lamina propria; and mice of CTB-UreB/4CTB chimeric protein group showed a very small amount of *Helicobacter pylori* colonization in the gastric pits, no macrophage and neutrophil infiltration on the tissue sections thereof (see FIG. 22).

3.3 Conclusion

Throughout the experiment, the mice receiving immunization of CTB-UreB/4CTB chimeric protein showed no adverse effects, pathological examination showed that immunized mice had no significant inflammatory changes in the stomach, which indicated that HP vaccine with CTB-UreB/4CTB chimeric protein as the antigen components has good security when being used for immunization with the test dose.

CTB-UreB/4CTB chimera protein by oral immunization can induce an effective immune response, has a good protective effect on the mice challenged with HP SSI bacteria challenge. Therefore it has a good prospect as an anti-HP infection oral vaccine.

The above results of the examples of detection showed that, oral administration of recombinant CTB-UreB fusion protein and CTB-UreB/4CTB chimeric protein can stimulate the body to produce specific antibodies against UreB antigen; wherein the titers and seroconversion rates of the serum specific IgG and stomach mucus s-IgA antibody obtained from CTB-UreB/4CTB chimeric protein immunized mice was significantly higher than that of CTB-UreB fusion protein, and there was a significant difference when as compared with the control group, indicating that the above antigens have good immunoreactivity and antigenicity, could be used as HP's candidate vaccine.

The results showed that antibody levels produced by CTB-UreB/4CTB chimeric protein were significantly higher than antibody generated by immunization with only UreB. And both for antibodies in serum and secretory antibodies, it was observed that CTB-UreB/4CTB chimeric protein induced a significant increase in antibodies levels. This indicates that the antigen composition of the present invention significantly improved the immunogenicity of the original antigen, and enhanced the body's immune response, contributes to the preparation of more effective vaccines. The results of secretory IgA test in Table 1 and FIG. 14 also showed that the chimera protein constructed with recombinant protein antigen of the present invention is in favor of the antigen to penetrate the intestinal mucosa and stimulate mucosal membrane to generate secretory IgA.

Comparative Example 1

The inventors constructed expression vector to express fusion protein of *H. pylori* antigens such as UreB and the $A_2$ subunit of cholera toxin (CTA 2), and combined the fusion protein with CTB protein expressed in vitro, to try to form chimera protein of UreB-CTA$_2$-/5CTB.

According to the prior art, the combination mode of CTA$_2$ with CTB and that of CTB themselves are all the non-covalent bonding, then the same method should have similar yield.

Figure 23A:
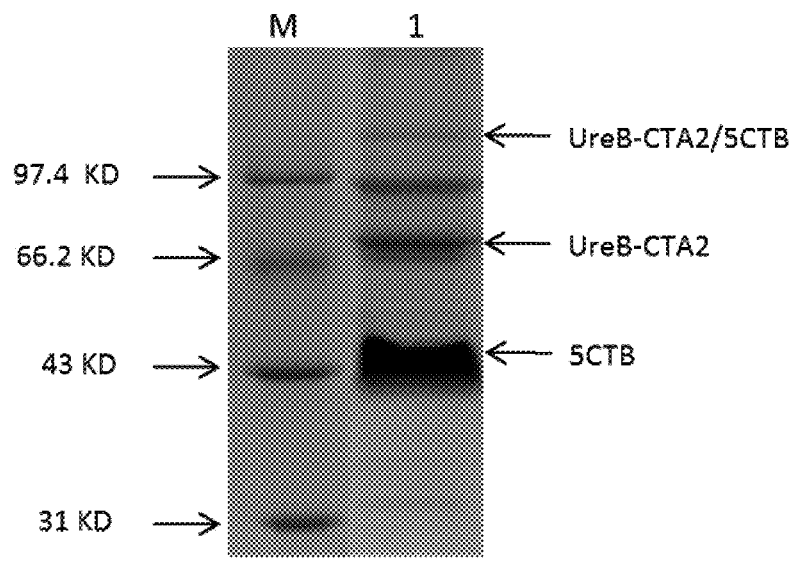
FIGS. 23A and 23B respectively are electrophoresis results for assembly efficiency comparison of UreB-CTA$_2$/5CTB and CTB-UreB/4CTB, lane 1 is the experimental results for Comparative Example 1 and lane 2 is the experimental results for the Example according to the invention.
Figure 23B:
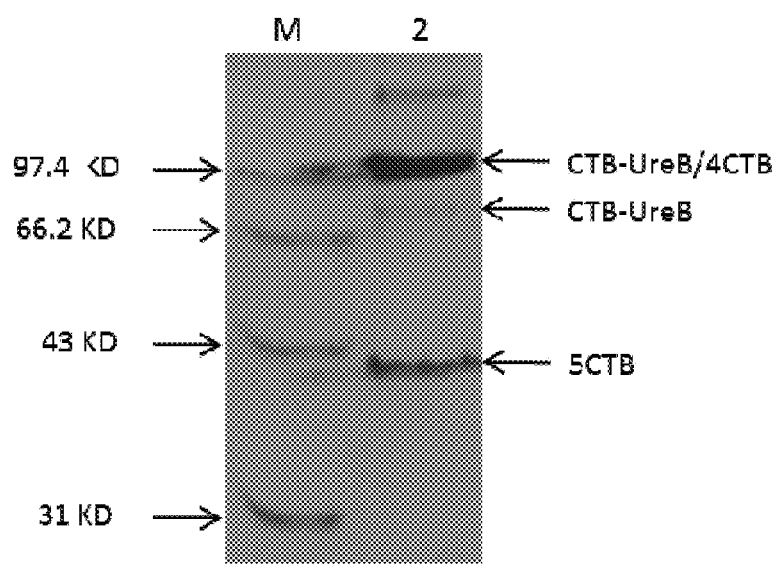

However, the results show that UreB-CTA$_2$/5CTB chimeric protein assembly efficiency <5% (see FIG. 23A), while CTB-UreB/4CTB chimeric protein assembly efficiency >90% (see FIG. 23B), assembling efficiency of CTB-UreB/4CTB of the present invention is much higher than assembly efficiency of UreB-CTA$_2$/5CTB. CTB-UreB/4CTB chimeric protein can significantly overcome the defect of low possibility of scaled production of UreB-CTA$_2$/5CTB due to the low efficiency of the assembly thereof.

Comparative Example 2

The inventors tried to use yeast as a represent for eukaryotic expression systems for the simultaneous expression CTB-antigen fusion proteins and CTB, wished to get the naturally formed chimeric structure with desired effect. The inventors found that, when expressed in yeast systems, CTB could correctly form a homo-pentameric structure composed of five identical CTB monomer, but the molecular weight of the expressed CTB (about 65 KD) was significantly greater than that of the natural state (55 KD), which suggested that when expressed in eukaryotic systems, the CTB glycosylation may have occurred as the post-translational modifications, there is a big difference between the expressed CTB and the native CTB molecule, thereby adversely effected the binding force with GM1 receptor. At the same time, when chimera was prepared in this manner, there are strict size requirements to the antigen to be fused with CTB. In addition, when expressed with this mode, the efficiency for natural assembly of fusion protein and CTB is low, resulting in the expression of the entire system has a very low yield, and thus does not applicable to large-scale preparation of a vaccine.

Comparative Example 3

The inventors had tried to express CTB-antigen fusion protein and CTB simultaneously in *Escherichia coli* as the representative for a prokaryotic expression system, wishing to get the natural formation of chimeras. Since pentameric assembly mechanism of cholera toxin B subunit is unknown, it's currently agreed among various studies that the assembly of chimeras occurs in penetrating process. In *E. coli* expression system, CTB-antigen fusion protein with the signal peptide cannot properly penetrate the cell membrane, and form the desired chimeric structure. Furthermore, most of the fusion protein expressed in intracellular form inclusion bodies, CTB cannot form a natural CTB pentamer either due to the presence of starting amino acid methionine, and therefore cannot form the desired chimeric structure.

The above description just takes *H. pylori*-associated antigen as an example to indicate the application and effects of the CTB-X-4CTB system of the present invention on enhancing the immunogenicity of the antigen. Based on experience and understanding of the skilled in the art, it can be inferred CTB-X-4CTB system of the present invention can also be applied to a variety of other mucosal immune antigens, including but not limited to *H. pylori* antigens, typhoid antigen, influenza HA antigen, to improve the immunogenicity of these antigens, and prepare high-potency vaccine. The corresponding carrier selection and preparation, expression and purification of proteins are known technology in the art, those of ordinary skill in the art after understanding the point of the present invention, can utilize the CTB-X-4CTB system of present invention to prepare the corresponding fusion proteins and antigen composition, and detecting the corresponding increase of immunogenicity.

Therefore, the above description is only preferred embodiments of the present invention, it is not intended to limit the present invention. Within the spirit and principles of the present invention, any modifications, equivalent substitutions and improvements should be included within the scope of protection of the present invention.

What is claimed is:

1. An antigen chimera, comprising: a fusion protein of an antigen and a mucosal immune adjuvant protein monomer capable of forming a multimer; and the mucosal immune adjuvant protein monomer capable of forming the multimer;

wherein the mucosal immune adjuvant protein monomer capable of forming the multimer is one selected from cholera toxin B subunit (CTB) and *E. coli* heat-labile enterotoxin B subunit (LTB), the multimer is a pentamer, and in the chimera the molar ratio between the fusion protein and the mucosal immune adjuvant protein monomer capable of forming the multimer is 1:4, wherein the pH in which the antigen chimera is stable is greater than 7.0, wherein the antigen is at least one selected from *Helicobacter pylori* urease B subunit (UreB), *Helicobacter pylori* cytotoxin associated gene A (CagA) and *Helicobacter pylori* neutrophil activating protein (NAP), wherein the antigen chimera is produced with prokaryotic expression vectors, wherein the antigen is fused to the C-terminus of the mucosal immune adjuvant protein monomer by a flexible protein linker.

2. The antigen chimera according to claim 1, wherein the cholera toxin B subunit and *E. coli* heat-labile enterotoxin B subunit of the antigen chimera are in their natural structure or a mutant capable of forming the pentamer.

3. The antigen chimera according to claim 1, wherein the fusion protein comprises three-G4S (SEQ ID NO: 4) linkers located between the antigen and the mucosal immune adjuvant protein monomer.

4. A process for preparing a chimera by renaturation, the chimera comprising (1) a fusion protein of a protein with a protein monomer capable of forming a multimer and (2) the protein monomer capable of forming the multimer, the chimera is formed by fusion of the protein monomer of (1) the fusion protein and (2) the protein monomer to form the multimer, the method comprising:

pre-refolding the (2) protein monomer capable of forming the multimer in a buffer solution containing 6M to 9M of urea, and with a pH of 3.0 to 4.0 for 0.5 to 3 hours; and refolding the (1) fusion protein and (2) the protein monomer capable of forming the multimer in a refolding solution containing 1.0M to 2.5M of urea and 0.2 mM to 1.0 mM of DTT or mercaptoethanol for the formation of the chimera, the pH of the refolding solution being greater than 7.0, wherein the chimera is the antigen chimera according to claim 1.

5. The process according to claim 4, wherein the buffer solution contains 8M of urea.

6. The process according to claim 4, wherein the (2) protein monomer capable of forming the multimer is pre-refolded for 1 hour.

7. The process according to claim 4, wherein the pH of the refolding solution is pH 8.0.

8. The antigen chimera according to claim 1, wherein the pH in which the antigen chimera is stable is pH 8.0.

9. The antigen chimera according to claim 1, wherein the fusion protein is expressed from a DNA sequence selected from the group consisting of SEQ ID NO:1, SEQ ID NO:2, and SEQ ID NO:3.

* * * * *

SEQUENCE LISTING

```
<160> NUMBER OF SEQ ID NOS: 5

<210> SEQ ID NO 1
<211> LENGTH: 2067
<212> TYPE: DNA
<213> ORGANISM: Artificial Sequence
<220> FEATURE:
<223> OTHER INFORMATION: synthetic DNA

<400> SEQUENCE: 1
atgacacctc aaaatattac tgatttgtgt gcagaatacc acaacacaca aatacatacg      60
ctaaatgata agatattttc gtatacagaa tctctagctg gaaaaagaga gatggctatc     120
attactttta agaatggtgc aacttttcaa gtagaagtac caggtagtca acatatagat     180
tcacaaaaaa aagcgattga aaggatgaag gataccctga ggattgcata tcttactgaa     240
gctaaagtcg aaaagttatg tgtatggaat aataaaacgc ctcatgcgat tgccgcaatt     300
agtatggcaa atggtggtgg tggttctggt ggtggtggtt ctggtggtgg tggttctatg     360
aaaaagatta gcagaaaaga atatgtttct atgtatggcc ctactacagg cgataaagtg     420
agattgggcg atacagactt gatcgctgaa gtagaacatg actacaccat ttatggcgaa     480
gagcttaaat tcggtggcgg taaaactttg agagaaggca tgagccaatc caacaacccct     540 agcaaagaag aactggattt aatcatcact aacgctttaa tcgtggatta caccggtatt     600
tataaagcgg atattggtat taaagatggc aaaatcgctg gcattggcaa aggcggcaac     660
aaagacatgc aagatggcgt taaaaacaat cttagcgtgg gtcctgctac tgaagcctta     720
gctggtgaag gtttgatcgt aactgctggt ggtattgaca cacacatcca cttcatctcc     780
ccccaacaaa tccctacagc ttttgcaagc ggtgtaacaa cgatgattgg tggcggaact     840
ggccctgctg atggcactaa cgcaaccact atcactccag gcagaagaaa tttaaaatgg     900
atgctcagag cggctgaaga atattctatg aatttaggtt tcttagctaa aggtaacgct     960
tctaatgatg cgagcttagc cgatcaaatt gaagccggtg cgattggctt taaaatccat    1020
gaagactggg gaacaactcc ttctgcaatc aatcatgcgt tagatgttgc ggacaaatac    1080
gatgtgcaag tcgctatcca tacggacact ttgaatgaag ccggttgtgt agaagacact    1140
atggcagcca ttgccggacg cactatgcac actttccaca ctgaaggcgc tggtggcgga    1200
cacgctcctg atatcattaa agtagccggc gaacacaaca ttctgcccgc ttccactaac    1260
cccactatcc ctttcactgt gaatacagaa gcagaacaca tggacatgct tatggtgtgc    1320
```

| | |
|---|---|
| caccacttgg ataaaagcat taagaagat gttcagttcg ctgattcaag gatccgccct | 1380 |
| caaaccattg cggctgaaga cactttgcat gacatgggga ttttctcaat cactagttct | 1440 |
| gactctcaag ctatgggtcg tgtgggtgaa gttatcacca gaacttggca aacagctgac | 1500 |
| aaaaacaaaa aagaatttgg ccgcttgaaa gaagaaaaag gcgataacga caacttcaga | 1560 |
| atcaaacgct acttgtctaa atacaccatt aacccagcga tcgctcatgg gattagcgag | 1620 |
| tatgtaggtt ctgtagaagt gggcaaagtg gctgacttgg tattgtggag tccagcattc | 1680 |
| tttggcgtga acccaacat gatcatcaaa ggtgggttta ttgcattgag tcaaatgggc | 1740 |
| gatgcgaacg cttctatccc taccccacaa ccagtttatt acagagaaat gttcgctcat | 1800 |
| catggtaaag ccaaatacga tgcaaacatc acttttgtgt ctaaagcggc ttatgacaaa | 1860 |
| ggcattaaag aagaattagg gcttgaaaga caagtgttgc cggtaaaaaa ttgcagaaac | 1920 |
| atcactaaaa aagacatgca attcaacgac actaccgctc acattgaagt caatcctgaa | 1980 |
| acttaccatg tgttcgtgga tggcaaagaa gtaacttcta aaccagccac taaagtgagc | 2040 |
| ttggcgcaac tctttagcat tttctaa | 2067 |

<210> SEQ ID NO 2
<211> LENGTH: 1269
<212> TYPE: DNA
<213> ORGANISM: Artificial Sequence
<220> FEATURE:
<223> OTHER INFORMATION: Synthetic DNA

<400> SEQUENCE: 2

| | |
|---|---|
| atgacacctc aaatattac tgatttgtgt gcagaatacc acaacacaca aatacatacg | 60 |
| ctaaatgata agatattttc gtatacagaa tctctagctg aaaaagaga gatggctatc | 120 |
| attacttta agaatggtgc aacttttcaa gtagaagtac caggtagtca acatatagat | 180 |
| tcacaaaaaa aagcgattga aaggatgaag gataccctga ggattgcata tcttactgaa | 240 |
| gctaaagtcg aaaagttatg tgtatggaat aataaaacgc tcatgcgat tgccgcaatt | 300 |
| agtatggcaa atggtggtgg tggttctggt ggtggtggtt ctggtggtgg tggttctatg | 360 |
| aaattatttg gaaattccaa taacaataat aatggactca aaaacgaacc catttacgct | 420 |
| caagttaata aaaagaaagc aggacaagca actagccctg aagagcccat ttacgctcaa | 480 |
| gttgctaaaa aggtgagtgc aaaaattgac caactcaacg aagctacatc agcaataaat | 540 |
| agaaaaattg accggattaa caaaattgca tcagcaggta aaggagtggg cggtttcagt | 600 |
| ggagcagggc gatcagctag tcctgaaccc atttacgcta caattgattt tgatgaggca | 660 |
| aatcaagcag gcttccctct taggagaagc actgcagtta atgatctcag taaagtaggg | 720 |
| cttcaaggg aacaagaatt gactcgtaga attggcgatc tcaatcaggc agtgtcagaa | 780 |
| gctaaaacag gtcattttga caaactagaa caaagatgg atgaactcaa agattctaca | 840 |
| aaaaagaatg ctttgaagct atgggctgaa agcacgaaac aagtgcctac tggtttgcag | 900 |
| gcgaaattgg acaattacgc tactaacagc cacacacgca ttaacagtaa tgtccaaaat | 960 |
| ggagcagtca atgagaaagt gaccggtatg ctaacgcaaa aaaccctga gtggctcaag | 1020 |
| ctcgtgaatg ataagatagt tgcacataat gtgggaagcg ctcatttgtc agagtatgat | 1080 |
| aaaattggat tcaaccaaaa gaatatgaaa gattattctg attcgttcaa gttttccacc | 1140 |
| aagttgaaca atgccgtaaa agacattaag tctagctttg tgcaattttt aaccaataca | 1200 |
| ttttctacag gatcttacag cttgatgaaa gcaaatgcgg aacatggagt caaaaatact | 1260 |
| acaaaataa | 1269 |

```
<210> SEQ ID NO 3
<211> LENGTH: 792
<212> TYPE: DNA
<213> ORGANISM: Artificial Sequence
<220> FEATURE:
<223> OTHER INFORMATION: Synthetic DNA

<400> SEQUENCE: 3
atgacacctc aaaatattac tgatttgtgt gcagaatacc acaacacaca aatacatacg      60
ctaaatgata agatattttc gtatacagaa tctctagctg aaaaagaga gatggctatc     120 attacttta agaatggtgc aacttttcaa gtagaagtac caggtagtca acatatagat     180
tcacaaaaaa aagcgattga aaggatgaag gataccctga ggattgcata tcttactgaa     240
gctaaagtcg aaaagttatg tgtatggaat aataaaacgc tcatgcgat tgccgcaatt     300 agtatggcaa atggtggtgg tggttctggt ggtggtggtt ctggtggtgg tggttctatg     360
aaaacatttg aaattttaaa acatttgcaa gcggatgcga tcgtgttgtt tatgaaagtg     420
cataacttcc attggaatgt gaaaggcacg gatttttta atgtacataa agctactgaa     480
gaaatttatg aagagtttgc ggacatgttt gatgatctcg ctgaaaggat cgttcaatta     540
ggacaccacc ccttagtcac tttatccgaa gcgatcaaac tcactcgtgt taaagaagaa     600
actaaaacga gcttccactc taaagacatt tttaaagaaa ttctagagga ctataaacac     660
ctagaaaaag aatttaaaga gctctctaac accgctgaaa aagaaggcga taaagtcacc     720
gtaacttatg cggatgatca attggccaag ttgcaaaaat ccatttggat gctgcaagcc     780
catttagctt aa                                                        792

<210> SEQ ID NO 4
<211> LENGTH: 5
<212> TYPE: PRT
<213> ORGANISM: Artificial Sequence
<220> FEATURE:
<223> OTHER INFORMATION: linker

<400> SEQUENCE: 4

Gly Ser Ser Ser Ser
1               5

<210> SEQ ID NO 5
<211> LENGTH: 7
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (2)..(6)

<400> SEQUENCE: 5

Ala Glu Ala Ala Ala Lys Ala
1               5
```